(12) United States Patent
Kuzushima

(10) Patent No.: US 7,619,058 B2
(45) Date of Patent: Nov. 17, 2009

(54) EPITOPE/PEPTIDE RECOGNIZED BY HLA-A2402-RESTRICTED EP-CAM-SPECIFIC CTL AND USE OF THE SAME

(75) Inventor: Kiyotaka Kuzushima, Nagoya (JP)

(73) Assignees: Aichi Prefecture, Aichi (JP); Otsuka Pharmaceutical Co., Tokyo (JP)

(*) Notice: Subject to any disclaimer, the term of this patent is extended or adjusted under 35 U.S.C. 154(b) by 447 days.

(21) Appl. No.: 10/586,852

(22) PCT Filed: Jan. 19, 2005

(86) PCT No.: PCT/JP2005/000587

§ 371 (c)(1),
(2), (4) Date: Jul. 20, 2006

(87) PCT Pub. No.: WO2005/068632

PCT Pub. Date: Jul. 28, 2005

(65) Prior Publication Data

US 2009/0010951 A1    Jan. 8, 2009

(30) Foreign Application Priority Data

Jan. 20, 2004   (JP) .............................. 2004-011752

(51) Int. Cl.
C07K 5/00   (2006.01)
(52) U.S. Cl. ...................................... 530/300
(58) Field of Classification Search ................. None
See application file for complete search history.

(56) References Cited

U.S. PATENT DOCUMENTS

| | | | |
|---|---|---|---|
| 6,417,165 B1 | 7/2002 | Valmori et al. | |
| 6,664,232 B1 | 12/2003 | Itoh et al. | |
| 2002/0039583 A1 | 4/2002 | Subjeck et al. | |
| 2003/0148463 A1* | 8/2003 | Kufer et al. ................ | 435/69.1 |

FOREIGN PATENT DOCUMENTS

| | | |
|---|---|---|
| CA | 2 325345 A1 | 10/1999 |
| JP | 8-500103 A | 1/1996 |
| JP | 11-318455 A | 11/1999 |
| JP | 2000-116383 A | 4/2000 |
| JP | 2001-245675 A | 9/2001 |
| JP | 2002-510496 A | 4/2002 |
| JP | 2003-270 A | 1/2003 |
| JP | 2003-510334 A | 3/2003 |
| JP | 2003-533175 A | 11/2003 |
| WO | 94/03435 A1 | 2/1994 |
| WO | 97/15597 A1 | 5/1997 |
| WO | WO 97/15597 A1 | 5/1997 |
| WO | 00/06595 A1 | 2/2000 |
| WO | 01/23421 A2 | 4/2001 |
| WO | 01/36453 A2 | 5/2001 |
| WO | 03/012086 A1 | 2/2003 |
| WO | WO 03/012086 A1 | 2/2003 |

OTHER PUBLICATIONS

K.C. Parker et al., "Scheme for ranking potential HLA-A2 binding peptides based on independent binding of individual peptie side-chains", J. Immnol., vol. 152, pp. 163-175, (1974).
K.C. Parker, et al., "Scheme for ranking potential HLA-A2 binding peptides based on Independent binding of individual peptide side-chains", Journal of Immunology, 1994, 152: 163-175.
K. Tajima et al., "Identification of an epitope from the epithelial cell adhesion molecule eliciting HLA-A*2402-restricted-cytotoxic T-lymphocyte response", Tissue Antigens, 2004, 64:650-659.
G.V. Ullenhag et al., "Immunization of colorectal carcinoma patients with a recombinant canarypox virus expressing the tumor antigen Ep-CAM/KSA (ALVAC-KSA) and granulocyte macrophage colony-stimulating factor induced a tumor-specific cellular immune response", Clin. Cancer Res., 2003, 9(7):2447-2456.
Australian Office Action dated Oct. 5, 2007.
Australian Search Report 2005.
European Office Action dated Dec. 6, 2007.
Victor H. Englehard "Structure of Peptides Associated with Class I & II MHC Molecules", Annual Review of Immunology (1994), pp. 181-207.
Andreas Trojan et al., "Generation of Cytotoxic T Lymphocytes against Native and Altered Peptides of Human Leukocyte Antigen-A*0201 Restricted Epitopes from the Human Epithelial Cell Adhesion Molecule", Cancer Research (2001), pp. 4761-4765, vol. 61.
Elisabeth Ras et al., "Identification of Potential HLA-A *0201 Restricted CTL Epitopes Derived from the Epithelial Cell Adhesion Molecule (Ep-CAM) and the Carcinoembryonic Anitgen (CEA)" American Society for Histocompatibility & Immunogenetics (1997), pp. 81-89, vol. 53.

* cited by examiner

Primary Examiner—Misook Yu
(74) Attorney, Agent, or Firm—Sughrue Mion, PLLC

(57) ABSTRACT

A peptide consisting essentially of the amino acid sequence represented by SEQ ID NO:1; a peptide consisting essentially of the amino acid sequence represented by SEQ ID NO:2; or a mutant peptide consisting essentially of an amino acid sequence derived from the amino acid sequence represented by SEQ ID NO:1 or 2 by addition, deletion or substitution of one or more amino acids, the peptide being capable of forming a complex with an HLA-A2402 molecule to be recognized by HLA-A2402-restricted cytotoxic T lymphocytes or induce such lymphocytes. Such a peptide is useful as a cancer vaccine for epithelial cancer patients having HLA-A2402.

3 Claims, 5 Drawing Sheets

A

B

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 1

Arg Tyr Gln Leu Asp Pro Lys Phe Ile
1               5

<210> SEQ ID NO 2
<211> LENGTH: 10
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 2

Tyr Tyr Val Asp Glu Lys Ala Pro Glu Phe
1               5                   10

<210> SEQ ID NO 3
<211> LENGTH: 9
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 3

Asn Tyr Lys Leu Ala Val Asn Cys Phe
1               5

```
<210> SEQ ID NO 4
<211> LENGTH: 9
<212> TYPE: PRT
<213> ORGANISM: Artificial Sequence
<220> FEATURE:
<223> OTHER INFORMATION: SYNTHEIC PROTEIN EPITOPE PEPTIDE CANDIDATE

<400> SEQUENCE: 4

Leu Tyr Glu Asn Asn Val Ile Thr Ile
1               5

<210> SEQ ID NO 5
<211> LENGTH: 9
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 5

Leu Phe His Ser Lys Lys Met Asp Leu
1               5

<210> SEQ ID NO 6
<211> LENGTH: 10
<212> TYPE: PRT
<213> ORGANISM: Artificial Sequence
<220> FEATURE:
<223> OTHER INFORMATION: SYTHETIC PROTEIN EPITOPE PEPTIDE CANDIDATE

<400> SEQUENCE: 6

Lys Tyr Glu Lys Ala Glu Ile Lys Glu Met
1               5                   10

<210> SEQ ID NO 7
<211> LENGTH: 9
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 7

Glu Met Gly Glu Met His Arg Glu Leu
1               5

<210> SEQ ID NO 8
<211> LENGTH: 20
<212> TYPE: DNA
<213> ORGANISM: Artificial Sequence
<220> FEATURE:
<223> OTHER INFORMATION: SYNTHETIC DNA PRIMER

<400> SEQUENCE: 8
atggcgcccc cgcaggtcct                                              20

<210> SEQ ID NO 9
<211> LENGTH: 30
<212> TYPE: DNA
<213> ORGANISM: Artificial Sequence
<220> FEATURE:
<223> OTHER INFORMATION: SYNTHETIC DNA PRIMER

<400> SEQUENCE: 9
ttatgcattg agttccctat gcatctcacc                                   30

<210> SEQ ID NO 10
```

-continued

```
<211> LENGTH: 27
<212> TYPE: DNA
<213> ORGANISM: Artificial Sequence
<220> FEATURE:
<223> OTHER INFORMATION: SYNTHETIC DNA PRIMER

<400> SEQUENCE: 10
cgttatcaac tggatccaaa atttatc                                              27

<210> SEQ ID NO 11
<211> LENGTH: 30
<212> TYPE: DNA
<213> ORGANISM: Artificial Sequence
<220> FEATURE:
<223> OTHER INFORMATION: SYNTHETIC DNA PRIMER

<400> SEQUENCE: 11
tattatgttg atgaaaaagc acctgaattc                                           30

<210> SEQ ID NO 12
<211> LENGTH: 11
<212> TYPE: PRT
<213> ORGANISM: Artificial Sequence
<220> FEATURE:
<223> OTHER INFORMATION: SYNTHETIC PROTEIN EPITOPE PEPTIDE CANDIDATE

<400> SEQUENCE: 12

Tyr Gln Leu Asp Pro Lys Phe Ile Thr Ser Ile
1               5                   10
```

EPITOPE/PEPTIDE RECOGNIZED BY HLA-A2402-RESTRICTED EP-CAM-SPECIFIC CTL AND USE OF THE SAME

This Application is a 371 of PCT/JP2005/000587, filed Jan. 19, 2005; the disclosure of which is incorporated herein by reference.

TECHNICAL FIELD

The present invention relates to epitope peptides recognized by HLA-A2402-restricted cytotoxic T lymphocytes, antigen-presenting cells and major histocompatibility antigen complexes; cancer vaccines or cytotoxic T lymphocyte inducers comprising these as an active ingredient; passive immunotherapy drug for epithelial cancers comprising as an active ingredient such a cytotoxic T lymphocyte inducer; cancer treatment or amelioration methods using these; and methods of quantifying HLA-A2402-restricted cytotoxic T lymphocytes specific to cancers.

BACKGROUND ART

Cytotoxic T lymphocytes (hereinafter referred to as "CTL"s) are considered to be an important factor counteracting cancers.

The infiltration of CTLs exhibiting cytotoxicity against tumor cells at tumor sites of a cancer patient can be observed. A tumor antigen, which is a molecule targeted by such tumor specific CTLs, is broken down in a cell into peptides (tumor epitope peptides) comprising 8 to 11 amino acids, binds to a human leukocyte antigen (hereinafter referred to as "HLA") which is a major histocompatibility antigen, and is then presented on the surface of a tumor cell. CTLs recognize complexes comprising HLA and the tumor antigen peptide, and attack tumor cells. CTLs thus recognize tumor cells through the tumor antigen's HLA restriction.

HLAs are cell membrane antigens expressed on almost all cells, and are broadly classified into Class I antigens and Class II antigens. HLAs recognized together with epitope peptides by CTLs are classified as Class I antigens. HLA Class I antigens are further classified as HLA-A, HLA-B, HLA-C, etc., and their genes have subtypes. For example, HLA-A is polymorphous and has A1, A2, A24, A26, etc. subtypes. HLAs for each human individual are not therefore always identical, and CTLs can even recognize these HLA subtypes when recognizing a complex of an HLA Class I antigen and a tumor epitope peptide. Further, epitope peptides capable of binding to HLAs are known to have a peptide sequence motif (patterned sequence) capable of binding to one of each type of HLAs. Accordingly, for induction and/or activation of CTLs, it is essential to select peptides comprising the motif capable of binding to different types of HLAs for every patient.

Ep-CAM is a molecule widely expressed on the surface of cancer cells of epithelial origin, and acts as an intermediary for non-calcium dependent cell-to-cell adhesion. Ep-CAM is also known as EGP-2, 17-1A, GA733-2, or KSA. Ep-CAM is highly expressive in many tumors derived from various histological origins such as the large intestine, lungs, head and neck, mammary glands, etc., and its expression is regional in normal epithelial cells. Further, since tumor progression and Ep-CAM expression level correlate, the detection of Ep-CAM expression is useful as a marker for diagnosing minimally present tumor metastases and in predicting a patient's prognosis.

Ep-CAM is widely expressed in cancer cells that originate from epithelial cells, but is expressed locally in normal cells. Given this, Ep-CAM is an important target in immunotherapies and gene therapies with monoclonal antibodies.

For example, it is reported that the administration of an Ep-CAM-specific murine monoclonal antibody (designated as 17-1A) to patients whose tumors had been surgically removed was effective in the prophylaxis of distant metastasis, and that 7 consecutive years of administration was effective in improving survival rates. It has also been reported that Ep-CAM-specific monoclonal antibodies designated as 17-1A are effective in reducing mortality rate and tumor recurrence when used for treating patients with large intestine cancers.

Furthermore, some recent reports disclose the fact showing the possibility of cancer treatments using CTLs targeting HLA-restricted Ep-CAM.

For example, Patent document 1 reports that HLA-A0201-restricted Ep-CAM-specific CTLs destroy epithelial tumor cells, but do not affect normal cells. Patent document 1 discloses a peptide consisting of the YQLDPKFITSI sequence represented by SEQ ID NO: 12 as an Ep-CAM 174-184 epitope peptide recognized by HLA-A0201-restricted CTLs.

T-cell response to Ep-CAM is also observed in colon and large intestine cancer patients who do not receive immunotherapy. In addition, when large intestine cancer patients are immunized with Ep-CAM expressing recombinant canary pox virus, anti Ep-CAM-specific CTL response is derived without causing autoimmune response.

Among HLA-A types in HLA Class I antigens, HLA-A24 is expressed the most among Japanese people. Consequently, HLA-A24-restricted Ep-CAM epitope peptides are presumably desirable cancer vaccines. Reported as such epitope peptides are, for example, as follows.

Patent document 2 discloses 5 types of epitope peptides, consisting of the amino acid sequence containing 9 amino acid residues, derived from SART-2 tumor antigen proteins as an HLA-A2402-restricted CTL epitope peptide.

Patent document 3 discloses 6 types of epitope peptides, consisting of the amino acid sequence containing 8 to 11 amino acid residues, derived from ART-4 tumor antigen proteins as an HLA-A2402-restricted CTL epitope peptide.

Patent document 4 discloses 7 types of epitope peptides, consisting of the amino acid sequence containing 8 to 11 amino acid residues, derived from p56luk proteins (tumor antigen proteins coded by luk gene) abnormally expressed in large intestine cancer cells and small cell lung cancer cells as an HLA-A2402-restricted CTL epitope peptide obtained from a cell line established from an esophagus cancer patient.

Patent document 5 discloses 4 types of PI-9-derived peptides, consisting of the amino acid sequence containing 9 to 10 amino acids, obtained from KE4 tumor cell line-derived cDNA library as an HLA-A2402-restricted CTL epitope peptide obtained from a cell line established from an esophagus cancer patient.

Patent document 6 discloses 17 types of epitope peptides, consisting of the amino acid sequence containing 9 to 10 amino acids, of PI-9-derived peptides obtained from a 11 to 18 pulmonary adenocarcinoma cell line cDNA library as an HLA-A2402-restricted CTL epitope peptide obtained from a cell line established from a lung cancer patient.

Patent document 7 discloses an epitope peptide which consists of 9 to 10 amino acid residues, has a motif capable of binding to HLA-A24.1 (HLA-A2402), and has a first conserved residue of Y, F, or W toward the N-terminal, and a second conserved residue of F, I, W or M toward the C-terminal, wherein the first and second conserved residues are separated by 6 to 7 residues.

As exemplified above, various HLA-A2402-restricted CTL epitopes among tumor-related antigens have been identified; however the expression of tumor antigens varies depending on histological origins, individual cancer patient and each patient's lesion, and therefore further new epitopes are expected to be specified.

Further, since CTL derivation by Ep-CAM epitope peptide capable of binding to an HLA-A2402 molecule has not yet been confirmed, there is demand for developing new cancer cell-specific Ep-CAM epitope peptides capable of binding to an HLA-A2402 molecule, and capable of inducing CTLs.

Patent Document 1:
International Patent Publication No. WO97/15597
Patent Document 2:
Unexamined Japanese Patent Application Publication No. 1999-318455
Patent Document 3:
Unexamined Japanese Patent Application Publication No. 2000-116383
Patent Document 4:
International Patent Publication No. WO2000-06595
Patent Document 5:
Unexamined Japanese Patent Application Publication No. 2001-245675
Patent Document 6:
Unexamined Japanese Patent Application Publication No. 2003-270
Patent Document 7:
Unexamined Japanese Patent Application Publication No. 1996-500103 (claim 11, etc.)

DISCLOSURE OF THE INVENTION

Problems to be Solved by the Invention

Objects of the present invention are to provide Ep-CAM epitope peptides capable of inducing HLA-A2402-restricted cytotoxic T lymphocytes, antigen-presenting cells and major histocompatibility antigen complexes; cancer vaccines or cytotoxic T lymphocyte inducers comprising these as an active ingredient; Ep-CAM-specific HLA-A2402-restricted cytotoxic T lymphocytes; passive immunotherapy drugs comprising such lymphocytes; cancer treatment or amelioration methods using these; and methods of quantifying epithelial cancer-specific HLA-A2402-restricted cytotoxic T lymphocytes.

Means for Solving the Problems

For achieving the above objects, the present inventors predicted and synthesized 7 peptide sequences in Ep-CAM proteins by a bioinformatics approach to find epitope peptide sequences having the ability to bind to an HLA-A2402 molecule, which is the most common type in HLA-As (more than 60%) in the Japanese population, and about 20% in the European population.

When predicting peptides capable of binding to a specific HLA molecule by a bioinformatics approach, cytotoxic T lymphocytes induced by such predicted peptides in reality often do not recognize antigens comprising such peptides.

Under such circumstances, the present inventors found that CTL clones specific to two out of seven predicted epitope peptides actually exhibit cytotoxicity to HLA-A2402 positive Ep-CAM expressing cancer cells, but do not exhibit cytotoxicity to HLA-A2402 negative cancer cells.

Further, a cold target inhibition assay demonstrated that these epitope peptides are processed and presented as antigens on HLA-A2402 positive Ep-CAM positive cancer cells.

Consequently, these two epitope peptides can be used as cancer vaccines for people having HLA-A2402.

The present invention has been accomplished based on the above findings, and provides the following epitope peptides and the like.

Item 1. A peptide of any one of (1) to (4) below:
(1) a peptide consisting essentially of the amino acid sequence represented by SEQ ID NO: 1
(2) a peptide consisting essentially of the amino acid sequence represented by SEQ ID NO: 2
(3) a mutant peptide consisting essentially of an amino acid sequence derived from the amino acid sequence represented by SEQ ID NO:1 by addition, deletion or substitution of one or more amino acids, the peptide being capable of forming a complex with an HLA-A2402 molecule to be recognized by HLA-A2402-restricted cytotoxic T lymphocytes or induce such lymphocytes
(4) a mutant peptide consisting essentially of an amino acid sequence derived from the amino acid sequence represented by SEQ ID NO:2 by addition, deletion or substitution of one or more amino acids, the peptide being capable of forming a complex with an HLA-A2402 molecule to be recognized by HLA-A2402-restricted cytotoxic T lymphocytes or induce such a lymphocytes.

Item 2. A peptide of either (1) or (2):
(1) a peptide consisting essentially of the amino acid sequence represented by SEQ ID NO: 1
(2) a peptide consisting essentially of the amino acid sequence represented by SEQ ID NO: 2.

Item 3. A cancer vaccine comprising the peptide of Item 1 or 2 as an active ingredient.

Item 4. A cancer vaccine of Item 3, wherein the cancer is an epithelial cancer.

Item 5. A cancer vaccine of Item 3 or 4, wherein the cancer is selected from the group consisting of large intestinal cancers, lung cancers, breast cancers, gastric cancers, buccal cancers, pancreatic cancers, esophageal cancers, nasopharyngeal cancers, uterine cancers, prostate cancers, and gallbladder cancers.

Item 6. A cancer vaccine of any one of Items 3 to 5 which is used for a human having HLA-A2402 as a leukocyte antigen.

Item 7. A cytotoxic T lymphocyte inducer comprising the peptide of Item 1 or 2 as an active ingredient.

Item 8. A cytotoxic T lymphocyte inducer of Item 7 which is used for human having HLA-A2402 as a leukocyte antigen.

Item 9. A polynucleotide of any one of (5) to (8) below:
(5) a polynucleotide consisting essentially of the base sequence represented by SEQ ID NO:10
(6) a polynucleotide consisting essentially of the base sequence represented by SEQ ID NO:11
(7) a mutant polynucleotide that hybridizes with a polynucleotide consisting of the base sequence represented by SEQ ID NO:10 under stringent conditions, and coding for a peptide capable of forming a complex with an HLA-A2402 molecule to be recognized by HLA-A2402-restricted cytotoxic T lymphocytes or induce such lymphocytes
(8) a mutant polynucleotide that hybridizes with a polynucleotide consisting of the base sequence represented by SEQ ID NO: 11 under stringent conditions, and being capable of forming a complex with an HLA-A2402 molecule to be recognized by HLA-A2402-restricted cytotoxic T lymphocytes or induce such lymphocytes.

Item 10. A gene therapy drug for an epithelial cancer comprising the polynucleotide of Item 9 as an active ingredient.

Item 11. A recombinant vector comprising the polynucleotide of Item 9.

Item 12. A transformant wherein the recombinant vector of Item 11 is introduced.

Item 13. A process for producing the peptide of Item 1 or 2, comprising the steps of cultivating the transformant of Item 12, and collecting the peptide of Item 1 or 2 from the culture.

Item 14. An antigen-presenting cell which was pulsed with the peptide of Item 1 or 2.

Item 15. A cancer vaccine comprising the antigen-presenting cell of Item 14 as an active ingredient.

Item 16. A cancer vaccine of Item 15, wherein the cancer is an epithelial cancer.

Item 17. A cancer vaccine of Item 15 or 16, wherein the cancer is selected from the group consisting of large intestinal cancers, lung cancers, breast cancers, gastric cancers, buccal cancers, pancreatic cancers, esophagal cancers, nasopharyngeal cancers, uterine cancers, prostate cancers, and gallbladder cancers.

Item 18. A cancer vaccine of any one of Items 15 to 17 which is used for a human having HLA-A2402 as a leukocyte antigen.

Item 19. A cytotoxic T lymphocyte inducer comprising the antigen-presenting cell of Item 14 as an active ingredient.

Item 20. A cytotoxic T lymphocyte inducer of Item 19 which is used for treating a human having HLA-A2402 as a leukocyte antigen.

Item 21. A major histocompatibility antigen complex comprising a major histocompatibility antigen, and the peptide of Item 1 or 2 or the tumor antigen epitope peptide present on the antigen-presenting cell of Item 14.

Item 22. A major histocompatibility antigen complex of Item 21 comprising an HLA-A2402 molecule, a β2-microgloblin, and the peptide of Item 1 or 2 or the tumor antigen epitope peptide present on the antigen-presenting cell of Item 14.

Item 23. A cancer vaccine comprising the major histocompatibility antigen complex of Item 21 or 22 as an active ingredient.

Item 24. A cancer vaccine of Item 23, wherein the cancer is an epithelial cancer.

Item 25. A cancer vaccine of Item 23 or 24, wherein the cancer is selected from the group consisting of large intestinal cancers, lung cancers, breast cancers, gastric cancers, buccal cancers, pancreatic cancers, esophagal cancers, nasopharyngeal cancers, uterine cancers, prostate cancers, and gallbladder cancers.

Item 26. A cancer vaccine of any one of Items 23 to 25, which is used for treating a human having HLA-A2402 as a leukocyte antigen.

Item 27. A cytotoxic T-lymphocyte inducer comprising the major histocompatibility antigen complex of Item 21 or 22 as an active ingredient.

Item 28. A cytotoxic T lymphocyte inducer of Item 27 which is used for treating a human having HLA-A2402 as a leukocyte antigen.

Item 29. A major histocompatibility antigen complex tetramer comprising a major histocompatibility antigen and the peptide of Item 1 or 2 or the tumor antigen epitope peptide present on the antigen-presenting cell of Item 14.

Item 30. A cytotoxic T lymphocyte which is obtained by stimulating peripheral blood lymphocytes using one or more of (a) to (d) below:
(a) the peptide of Item 1 or 2
(b) the antigen-presenting cell of Item 14
(c) the major histocompatibility antigen complex of Item 21 or 22
(d) the major histocompatibility antigen complex tetramer of Item 29.

Item 31. A cytotoxic T lymphocyte of Item 30 which is obtained by the steps of forming a complex between a major histocompatibility antigen complex and/or a tetramer thereof and a cytotoxic T lymphocyte by stimulating peripheral blood lymphocytes using one or more of (a) to (d) defined in Item 30, and isolating the cytotoxic T lymphocyte from the complex.

Item 32. A passive immunotherapy drug comprising the cytotoxic T lymphocyte of Item 30 or 31 as an active ingredient.

Item 33. A passive immunotherapy drug of Item 32, wherein the cancer is an epithelial cancer.

Item 34. A passive immunotherapy drug of Item 32 or 33, wherein the cancer is selected from the group consisting of large intestinal cancers, lung cancers, breast cancers, gastric cancers, buccal cancers, pancreatic cancers, esophagal cancers, nasopharyngeal cancers, uterine cancers, prostate cancers, and gallbladder cancers.

Item 35. A passive immunotherapy drug of any one of Items 32 to 34 which is used for a human having HLA-A2402 as a leukocyte antigen.

Item 36. A method of quantifying HLA-A2402-restricted cytotoxic T lymphocytes in peripheral blood, comprising the steps of
making one or more of the following (a) to (d) act on peripheral blood:
(a) the peptide of Item 1 or 2
(b) the antigen-presenting cell of Item 14
(c) the major histocompatibility antigen complex of Item 21 or 22
(d) the major histocompatibility antigen complex tetramer of Item 29, and
quantifying cytotoxic T lymphocytes in peripheral blood or cytokine produced by such cytotoxic lymphocytes.

Item 37. A cancer treatment and/or amelioration method comprising administrating one or more of the following (a) to (d) to a human having HLA-A2402 as a leukocyte antigen:
(a) the peptide of Item 1 or 2
(b) the antigen-presenting cell of Item 14
(c) the major histocompatibility antigen complex of Item 21 or 22
(d) the major histocompatibility antigen complex tetramer of Item 29.

Item 38. A cancer treatment or amelioration method comprising the steps of collecting mononuclear cell fraction from peripheral blood of a human patient having HLA-A2402 as a leukocyte antigen, culturing the mononuclear cell fraction with one or more of the following (a) to (d):
(a) the peptide of Item 1 or 2
(b) the antigen-presenting cell of Item 14
(c) the major histocompatibility antigen complex of Item 21 or 22
(d) the major histocompatibility antigen complex tetramer of Item 29, and
returning to the patient's blood the mononuclear cell fraction in which cytotoxic T lymphocytes are induced and/or activated.

Item 39. A method of inducing cytotoxic T lymphocytes comprising administrating one or more of the following (a) to (d) to a human having HLA-A2402 as a leukocyte antigen:
(a) the peptide of Item 1 or 2
(b) the antigen-presenting cell of Item 14
(c) the major histocompatibility antigen complex of Item 21 or 22
(d) the major histocompatibility antigen complex tetramer of Item 29.

Item 40. A cancer treatment or amelioration method comprising administrating the cytotoxic T lymphocyte of Item 30 or 31 to a human having HLA-A2402 as a leukocyte antigen.

Item 41. A major histocompatibility antigen complex tetramer of Item 21, wherein the tetramer is a complex comprising the HLA-A2402 molecule, β2 microgloblin, and the peptide of Item 1 or 2 or the tumor antigen epitope peptide present on the antigen-presenting cell of Item 14.

Item 42. A cancer vaccine comprising the histocompatibility antigen complex tetramer of Item 41 as an active ingredient.

Item 43. A cancer vaccine of Item 42, wherein the cancer is an epithelial cancer.

Item 44. A cancer vaccine of Item 42 or 43, wherein the cancer is selected from the group consisting of large intestinal cancers, lung cancers, breast cancers, gastric cancers, buccal cancers, pancreatic cancers, esophagal cancers, nasopharyngeal cancers, uterine cancers, prostate cancers, and gallbladder cancers.

Item 45. A cancer vaccine of any one of Items 42 to 44 which is useful for treating human having HLA-A2402 as a leukocyte antigen.

Item 46. A cytotoxic T lymphocyte inducer comprising the major histocompatibility antigen complex tetramer of Item 41.

Item 47. A cytotoxic T lymphocyte inducer of Item 46 which is useful for treating human having HLA-A2402 as a leukocyte antigen.

EFFECT OF THE INVENTION

The present invention provides epitope peptides which are derived from Ep-CAM molecules widely expressed on epithelial cancer cells and can be recognized by cytotoxic T lymphocytes restricted to HLA-A2402, which is the most common type of human leukocyte antigens among the Japanese population. Consequently, such epitope peptides can be used as cancer vaccines for treating widespread HLA-A2402-positive human epithelial cancers.

BRIEF DESCRIPTION OF THE DRAWINGS

FIG. 3A shows the $^{51}$Cr release assay showing the cytotoxicity of C27 (an Ep173-specific CTL clone) against T2-A24 in the presence of peptide Ep173 or control peptide EBV-LMP419.

FIG. 3B shows the inhibitory effect of anti-HLA-A24 monoclonal antibodies on the cytotoxicity of the Ep173-specific CTL clone (C27) against a HLA-A2402 positive cell line (PC9).

FIG. 3C shows the cytotoxicity of C27 in the presence of Ep173 based on the cold target inhibition assay.

BEST MODE FOR CARRYING OUT THE INVENTION

Figure 1:
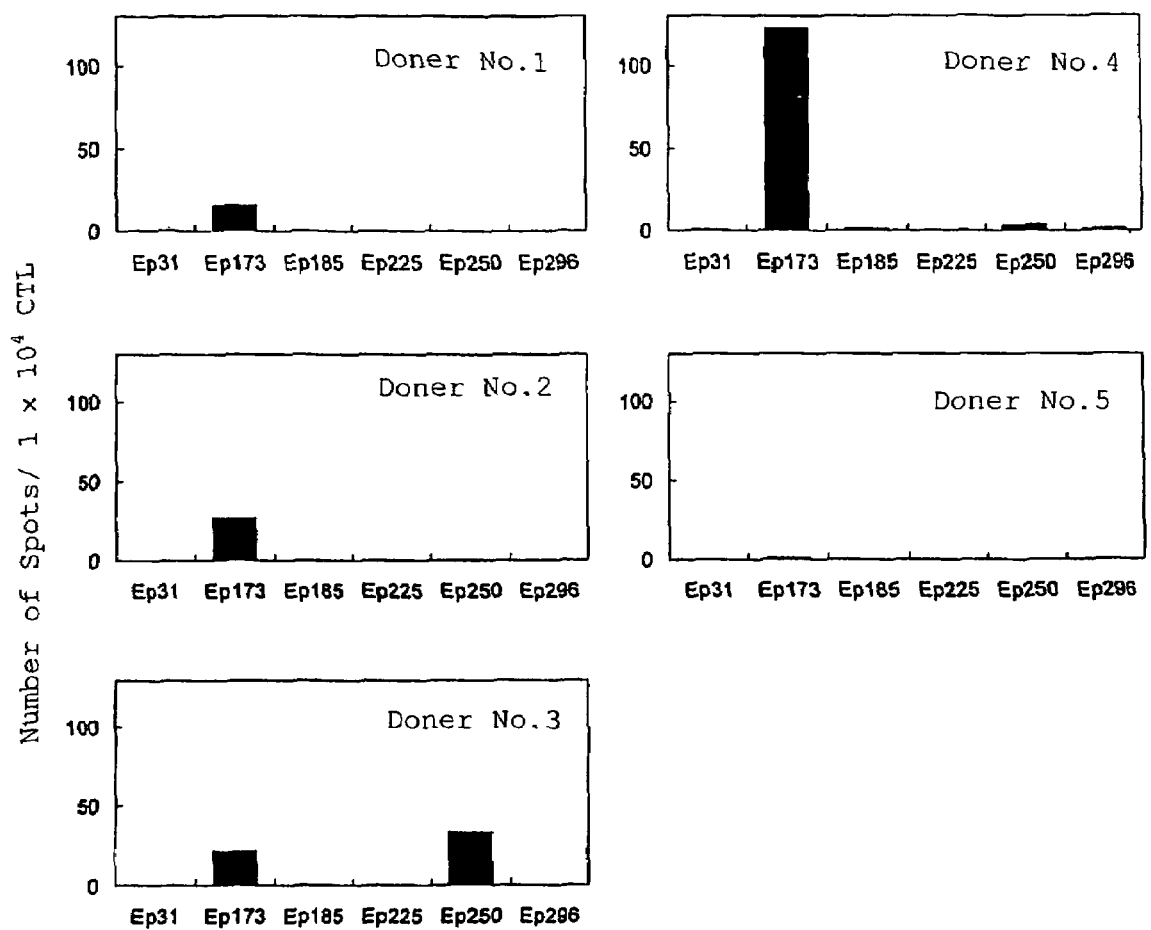
FIG. 1 shows the ELISOT assay evaluation results of a polyclonal peptide-activated CTL cell line.

The present invention is described in detail below.

(I) Epitope/Peptide

Structure

Peptides of the invention were confirmed to be epitope peptides recognized by cytotoxic T lymphocytes (hereinafter referred to as "CTL") as a result of screening potential peptides to be epitope peptides with reference to the HLA Peptide Binding Predictions, BioInformatics & Molecular Analysis Section (BIMAS), (bimas.dcrt.nih.gov/molbio/hla_bind/index.html), which is a reference site for searching epitope peptides consisting of 9 to 10 amino acids having an HLA-A2402-binding motif in amino acid sequences derived from the Ep-CAM protein widely expressed on cancer cells originating from epithelial cells.

More specifically, a peptide of the invention is any of (1) to (4) below:

(1) a peptide consisting essentially of the amino acid sequence represented by SEQ ID NO: 1, (2) a peptide consisting essentially of the amino acid sequence represented by SEQ ID NO: 2, (3) a mutant peptide consisting essentially of an amino acid sequence derived from the amino acid sequence represented by SEQ ID NO:1 by addition, deletion or substitution of one or more amino acids, the peptide being capable of forming a complex with an HLA-A2402 molecule to be recognized by HLA-A2402-restricted cytotoxic T lymphocytes or induce such lymphocytes, or (4) a mutant peptide consisting essentially of an amino acid sequence derived from the amino acid sequence represented by SEQ ID NO:2 by addition, deletion or substitution of one or more amino acids, the peptide being capable of forming a complex with an HLA-A2402 molecule to be recognized by HLA-A2402-restricted cytotoxic T lymphocytes or induce such a lymphocytes.

In the invention, peptide means a bioactive amino acid molecular chain in which α-amino groups and carboxy groups of adjacent amino acid residues are joined by peptide bonds.

In addition to the above-mentioned peptides, peptides also include salts and derivatives thereof inasmuch as their bioactivities are not deteriorated. Examples of such derivatives include those glucosylated, amidated, phosphorylated, carboxylated, phosphonated, formylated, acylated, etc. Preferable salts are acid-addition salts. Examples of such salts include hydrochloric acid-, phosphoric acid-, sulfric acid-, and like inorganic acid-addition salts; and formic acid-, acetic acid-, propionic acid-, tartaric acid-, and like organic acid-addition salts.

Peptides defined in (1) to (4) are each derived from Ep-CAM widely expressed on cancer cells originating from epithelial cells, and are recognized by HLA-A2402-restricted CTLs or induce or further activate such CTLs. Therefore, these peptides can be suitably used as CTL-inducing or activating tumor antigens, i.e. cancer vaccines, for treating or ameliorating human cancers having HLA-A2402. Further, these peptides can be used for preparing various tumor antigen epitope-specific peptides. Uses of peptides of the invention are described later.

The minimum number of amino acids in the mutant peptides defined in (3) and (4) is usually about 5, and preferably about 7. Maximum number of amino acids is not limited so long as the peptide can be recognized by an HLA-A2402-restricted CTL, and is usually about 12, with mutant peptides comprising about 9 to about 11 amino acids being preferable.

Such mutant peptides can be obtained by design the sequences for HLA-A2402-binding motifs with reference to the above-mentioned HLA Peptide Binding Predictions, and selecting therefrom those which can actually be recognized by HLA-A2402-restricted CTLs or induce such CTLs.

HLA-A2402 positive Ep-CAM epitope peptides can be identified, for example, by the following method.

Lymphocytes are isolated from HLA-A2402-positive adults and suspended in a RPMI1640 medium containing 10% human serum at a cell concentration of $2\times10^6$/ml. To each cell suspension is added one of the epitope-candidate peptides at a concentration of 1 µg/ml. The suspensions are incubated in a $CO_2$ incubator at 37° C. for 7 days, and IL-2 is added on day 7. Thereafter, A cycle of stimulation by the candidate peptide and stimulation by IL-2 is repeated once a week to induce Ep-CAM-specific CTLs.

It is determined by ELISPOT assay (Kuzushima K. et. al., The Journal of Clinical Investigation, (1999), Vol. 104, pages 163-171; etc.) whether or not the thus-induced epithelial cancer-specific CTLs are stimulated by the epitope-candidate peptides.

Using the above peptide candidates, a peptide library of peptides comprising about 20 amino acids is synthesized covering the entire Ep-CAM protein, ELISPOT assaying is conducted to the synthesized peptides, and the peptides to which CTLs respond are gradually shortened so that they ultimately comprise about 9 to about 10 amino acids to be used as epitope peptides of the invention.

Further, with regard to substitution of amino acids, a mutant peptide with an equivalent activity is likely to be obtained if an amino acid with electrical charge, solubility, hydrophilicity/hydrophobicity, polarity, and like properties similar to those of the pre-substituted amino acid is substituted so as to conserve the protein structure.

Methods for introducing deletions, additions (including insertions) and substitutions are well-known, and examples include Wurmer's technique (Science, 219,666 (1983)).

The peptide of the invention can be used in the form of complexes with addition of saccharides, polyethylene glycols, lipids, and the like, radioactive isotope derivatives and polymers, etc.

(II) Polynucleotides

The polynucleotide of the invention codes for the above peptide of the invention, and is specifically defined by any one of (5) to (8) below:

(5) a polynucleotide consisting essentially of the base sequence represented by SEQ ID NO:10, (6) a polynucleotide consisting essentially of the base sequence represented by SEQ ID NO:11, (7) a mutant polynucleotide that hybridizes with a polynucleotide consisting of the base sequence represented by SEQ ID NO:10 under stringent conditions, and coding for a peptide capable of forming a complex with an HLA-A2402 molecule to be recognized by HLA-A2402-restricted cytotoxic T lymphocytes or induce such lymphocytes, or (8) a mutant polynucleotide that hybridizes with a polynucleotide consisting of the base sequence represented by SEQ ID NO: 11 under stringent conditions, and being capable of forming a complex with an HLA-A2402 molecule to be recognized by HLA-A2402-restricted cytotoxic T lymphocytes or induce such lymphocytes.

Unless otherwise stated, polynucleotides of the invention encompass both DNA and RNA. DNA includes cDNA, genomic DNA and synthetic DNA. RNA includes mRNA, rRNA and synthetic RNA. In addition to polynucleotides having such base sequences, those complementary to such polynucleotides, and double-stranded polynucleotides are also included.

The polynucleotide of the base sequence represented by SEQ ID NO: 10, which is one of the polynucleotides coding for the amino acid sequence represented by SEQ ID NO:1, and the polynucleotide of the base sequence represented by SEQ ID NO: 11, which is one of the polynucleotides coding for the amino acid sequence represented by SEQ ID NO:2, are partial sequences of Ep-CAM gene obtained from human carcinoma-associated antigen GA733-2 (Szala, S. et. al., Proc. Natl. Acad. Sci. U.S.A. (1990) 87(9), 3542-3546).

The mutant polynucleotides defined in (7) and (8) are any of those usually comprising 15 or more, and preferably 21 or more, but usually 45 or less nucleotides in the region coding for the epitope peptide of the invention. Of these, polynucleotides comprising about 27 to about 33 nucleotides are preferable.

Taking DNA molecules as a representative example of polynucleotide molecules, "DNA molecules hybridizable with DNA molecules under stringent conditions" can be obtained by the methods described in, for example, *Molecular Cloning: A Laboratory Manual* (Sambrook et. al. edition, Cold Spring Harbor Laboratory Press, Cold Spring Harbor, N.Y., 1989), etc. In the present invention, "stringent conditions" refers to, for example, the conditions under which a positive hybridization signal hybridization is observed when heated at 42° C. in a solution of 6×SSC, 0.5% SDS, and 50% formamide, and washed in a solution of 0.1×SSC and 0.5% SDS at 68° C.

The mutant polynucleotides of (7) and (8) can be selected by confirming that the peptides expressed on the cells having HLA-A2402 using known protein expression systems are recognized by CTLs or have ability to induce CTLs by the methods described later.

The mutant polynucleotides have a 3' poly A structure, and the number of nucleotides of poly A of the polynucleotides is not limited since they do not affect the amino acid coding regions which act as tumor antigens.

The polynucleotide of the invention can provide useful gene information when preparing the epitope peptide of the invention using recombination techniques. Such a polynucleotide can be used as a nucleic acid reagent or standard polynucleotide.

(III) Recombinant Vector

The recombinant vector of the present invention is obtained by introducing the polynucleotide of the invention into a suitable vector DNA.

The vector DNA can be suitably selected in accordance with the kind of host cell and purpose of use. Vector DNAs may be those naturally present, or those naturally present but with partially missing DNA from regions not necessary for proliferation. Examples of vector DNAs include those originating from chromosomes, episomes, and viruses. More specifically, vector DNAs include those derived from bacteria plasmids, bacteriophages, transposons, yeast episomes, insertion elements, yeast chromosome elements, viruses (e.g. baculoviruses, papovaviruses, SV40, vacciniaviruses, adenoviruses, fowl pox viruses, pseudorabies viruses, retroviruses, etc.), etc., and combinations thereof, and those derived from genetic elements of plasmids and bacteriophages (e.g. cosmid, phargemid, etc.).

Further, expression vectors and cloning vectors can be used for biosynthesizing the peptides of the invention.

The recombinant vector has constituent elements of a gene sequence of object polynucleotide and gene sequences encoding information on replication and control (e.g. promoter, libosomal binding site, terminator, signal sequence, enhancer, etc.), and can be prepared by combining these sequences by known methods.

The polynucleotides of the invention can be inserted into vector DNAs by know methods. For example, DNA and vector DNA may be ligated at a specific site using a suitable restriction enzyme, and mixed for recombination using the ligase. Vector DNA can alternatively be obtained by ligating a suitable linker to the polynucleotide of the invention, and inserting the polynucleotide into a multicloning site of the vector DNA meeting the purpose of use.

(IV) Transformant

The transformant of the invention can be obtained by introducing the above recombinant vector, which contains the polynucleotide, to known host cells such as, for example, *Escherichia coli* (e.g. K12), bacteria belonging to the genus *Bacillus* (e.g. MI114), yeasts (e.g. AH22), insect cells (e.g. Sf cells), animal cells (e.g. COS-7 cells, Vero cells, CHO cells, etc.), etc. by know methods.

In view of good gene stability, a method for gene integration into a chromosome is preferable gene transfer method. An autonomous duplicate system using an extranuclear gene is a simple employable method. The transfer of vector DNA to a host cell can be performed by standard methods disclosed in, for example, *Molecular Cloning: A Laboratory Manual* (Sambrook et. al., Cold Spring Harbor Laboratory Press, Cold Spring Harbor, N.Y., 1989), etc. More specific examples include calcium phosphate transfection, DEAE-dextran mediation transfection, microinjection, cationic lipid-mediated transfection, electropolation, transduction, scrape loading, ballistic introduction, and infection, etc.

(V) Process for Producing Epitope Peptides

The peptide of the invention can be synthesized by known peptide synthesis methods such as solid phase peptide synthesis methods, and the like. Such peptide synthesis methods include those disclosed in *Peptide Synthesis* (Maruzen, 1975) and *Peptide Synthesis* (Interscience, New York, 1996). The epitope peptide of the invention can alternatively be produced using known chemical synthesis equipment such as peptide synthesizers manufactured by Applied Biosystems.

Further, the peptide of the invention can be prepared by a process comprising the steps of culturing the transformant of the invention described above, and collecting the peptide of the invention from this culture.

Such culturing can be performed by subculture or batch culture using a medium suitable for the host cell. Culturing can be continued until the peptide of the invention is produced in a desired amount, based on the peptide amount produced inside and outside the transformant, and/or the CTL inducing ability, which is one of the actions the peptide of the invention produced by the transformant exhibits.

It is preferable to further purify the peptide of the invention after collection from the culture medium. Purification can be performed by known methods such as molecular sieve chromatography, ion exchange chromatography, affinity chromatography, and like chromatographic techniques; combinations of fractioning means based on solubility differences using ammonium sulfate and/or alcohols, etc. Such purification can be carried out based on peptide recognition by CTLs or CTL induction by the peptide, more specifically for example, IFN-γ yield by CTLs.

Alternatively, the peptide of the invention in the culture medium can specifically be absorption-recovered using polyclonal or monoclonal antigens, which are produced based on the amino acid sequence of the peptide of the invention, and are specific to the amino acid sequence.

(VI) Antigen-Presenting Cells

The antigen-presenting cell of the invention is obtained by pulsing dendritic cells, macrophages, B lymphocytes, and like antigen-presenting cells with the peptide of the invention. The antigen-presenting cell of the invention is capable of expressing HLAs binding to the peptide of the invention on its surfaces, and has the ability to stimulate CTLs.

"Pulsing" is not limited, and can be performed, for example, by incubating such antigen-presenting cells in a medium containing the peptide of the invention at about 1 to 10 μg/ml at about 20 to about 30° C. for about 30 minutes to about 1 hour. Tumor antigen peptides recognized by HLA-A2402-restricted CTL are thereby presented on the antigen-presenting cell surface.

Tumor antigens refer to proteins, polypeptides or peptides present in tumor cells which are recognized by tumor-specific CTLs, or further induce CTLs or/and activate CTLs. Further, tumor antigen peptides refer to peptides produced by the decomposition of the tumor antigens in tumor cells, such peptide being recognized by CTLs, induce CTLs, or/and activate CTLs, when presented on cell surfaces as a result of binding to an HLA molecule.

The epitope sequence, derived from an amino acid sequence in a tumor antigen, and recognized by tumor-specific CTLs or further inducing or activating CTLs, is referred to as a tumor antigen epitope (tumor antigenic determinant).

In this specification, "recognize" means to sense and distinguish target from other substances, and, for example, bind to the target which are sensed. In this specification, "CTLs recognize tumor cells or tumor antigen epitope peptides" means that CTLs bind to human leukocyte antigens (HLA) or tumor antigen peptides through T-lymphocyte receptors.

"Activate" means to further enhance or stimulate a substance or state with a certain activity or action. In particular, "CTLs are activated" means that CTLs yield an effector such as, e.g. INF-γ or exhibit cytotoxicity against target cells they recognize when recognizing epitope peptides presented by HLAs.

"Induce" means to cause a certain activity or action from a substance or state having substantially no such activity or action. In particular, "inducing antigen-specific CTLs" means to differentiate and/or proliferate CTLs that specifically recognize a certain antigen in vitro or in vivo.

The antigen-presenting cell with which the epitope peptide of the invention is pulsed can be used as a cancer vaccine. The antigen-presenting cell can be further used for producing CTLs specific to epithelial-derived cancers, quantifying such CTLs in the human peripheral blood, etc.

(VII) Major Histocompatibility Antigen Complex

The major histocompatibility antigen complex of the invention is a complex between a major histocompatibility antigen and the peptide of the invention or the tumor antigen epitope peptide presented on an antigen-presenting cell surface to which the peptide of the invention is pulsed.

In the invention, the major histocompatibility antigen is a molecule that presents the peptide recognized by a T lymphocyte to a T lymphocyte antigen receptor, and is a human leukocyte antigen (HLA) recognized together with the epitope peptides by CTLs.

More specifically, the major histocompatibility antigen complex (hereinafter abbreviated to as "MHC") of the invention is a complex between MHC Class I human leukocyte antigen (HLA) expressed on target cell surfaces which are recognized together with the epitope peptide by CTLs; and the epitope peptide being recognized by CTLs or capable of inducing CTLs. Such complexes include those bound by β2-microgloblin.

Ep-CAM-specific CTL epitope peptides are the peptides of specific sites in Ep-CAM proteins, and are antigenic determinants recognized by CTLs and that immunologically bind to antigen receptors of CTLs. Further, CTL epitope peptides are able to eliminate cancer cells by directly attacking cells expressing Ep-CAM molecules.

In particular, MHCs of the invention refer to complexes between HLA-A2402 molecules expressed on target cells and certain epitope peptide in Ep-CAM proteins recognized by CTLs, and further may refer to such complexes with β2 microgloblin.

HLA-A2402 in the invention refers to an A-24 polymorphism, a subclass of Class I antigens, among human leukocyte antigens, and an HLA-A2402 molecule means an HLA-A2402 gene expressing product on an antigen-presenting cell surface.

Usable HLA-A2402 molecules are any HLA-A2402 molecules purified from culture of *E. coli* for HLA-A2402 expression, HLA-A2402 molecules forcedly expressed by transferring a gene into a target cell, and HLA-A2402 molecules naturally present on target cells. Further, HLA-A2402 molecules of the invention encompass fragments and heavy chains of HLA-A2402 molecules.

MHCs of the invention can be produced by various methods depending on their constituent elements, and may be formed by, for example, suspending the peptides of the invention, HLA-A2402 molecules and β2-microgloblin in a buffer such as Tris and the like, and incubating the suspension at about 4 to about 10° C. for about 24 to about 72 hours.

MHC may be a tetramer. MHC tetramer is a multimeric complex of four sub-complexes each comprising Ep-CAM epitope peptides recognized by CTLs and an HLA-A2402 molecule (usually a β2-microgloblin-bound HLA-A2402 molecule).

An MHC tetramer can be obtained by biotinylating MHC, and mixing streptavidin and the biotinylated MHC in a 1 to 4 ratio. Alternatively, MHC tetramer can be obtained by adding a biotin-binding site to a C-terminal of an HLA molecule, binding biotin to such a site after the formation of MHC, and then mixing streptavidin and the biotinylated MHC in a 1:4 ratio.

More specifically, MHC tetramer can be prepared, for example, in the following manner. For the preparation of MHC, HLA-A2402 molecule heavy chains and β2-microgloblin are produced in large amounts by using an *E. coli* recombinant protein expression system for MHC expression, and purified. An amino acid sequence recognizing biotin ligase is added beforehand at an HLA-A2402 heavy chain C-terminal. The purified HLA-A2402 heavy chain and β2-microgloblin are each dissolved in 8M urea. Added to 200 ml of a refolding buffer (pH 8.0; 100 mM Tris-HCl, 400 mM L-arginine-HCl, 2 mM EDTA, 0.5 mM oxidative glutathione, 5 mM reduced glutathione) are 12 mg of the peptide of the invention having the amino acid sequence represented by the sequence ID No:1 (RYQLDPKFI), 18.6 mg of HLA-A2402 heavy chains, and 13.2 mg of β2-microgloblin, each by using a syringe with a 27-gauge needle. The mixture is stirred in a bath at a temperature maintained at 10° C. for 48 to 72 hours to promote the formation of MHC. The refolding buffer containing MHC is subsequently dialyzed in a bath at a temperature maintained at 4° C. for 24 hours against 1.8 L distilled water, and the dialyzed refolding buffer is concentrated to 2 ml using a Centriprep 10 (Millipore Corporation, Bedford Mass.). MHC eluting with a molecular weight of about 45 kD is isolated by gel filtration chromatography using Superdex 200 HR (Amersham Pharmacia Biotech AB, Uppsala Sweden), thus producing the desired MHC tetramer.

For the subsequent preparation of biotinylated MHC, biotin is bound to a specific site of an HLA-A2402 heavy chain C-terminal by using biotin ligase (AVIDITY, LLC, Denver Colo.). The biotin-bound MHC is purified by gel filtration chromatography using Superdex 200 HR.

PE-labeled streptavidin (Molecular Probe, Eugene Oreg.) and the purified biotinylated MHC are then mixed in a molar ratio of 1 to 4, and MHC tetramer containing the amino acid sequence represented by the sequence ID NO:1 (RYQLDPKFI) that was eluted with a molecular weight of about 480 kD is isolated by gel filtration chromatography using Superdex 200 HR, concentrated to about 3 mg/ml using a Centricon 10 (Millipore Corporation), and maintained at 4° C. Preservatives such as sodium azide, EDTA, leupeptin and pepstatin may be added thereto.

In each preparation step mentioned above, it is desirable to purify the proteins and peptides to be used by known methods such as gel filtration chromatography.

MHC of the invention can be used as a cancer vaccine. Further, it can be used for producing epithelial cancer-specific CTLs, and for quantifying such CTLs in human peripheral blood.

(VIII) Cancer Vaccine, CTL Inducer and Gene Therapy Drug

Cancer Vaccine and CTL Inducer

The peptide of the present invention can be advantageously used as an active ingredient of a cancer vaccine for use in a passive immunotherapy with a vaccine. This cancer vaccine is usable for humans having HLA-A2402.

That is, administration of the peptide of the present invention to a cancer patient having HLA-A2402 as a leukocyte antigen induces or activates HLA-A2402-restricted CTLs that specifically recognize Ep-CAM, thereby making it possible to treat or ameliorate epithelial cancers and like diseases.

Since CTLs in cancer patients are a group of cells that recognizes two or more tumor antigens, use of multiple types of epitope peptides as a cancer vaccine sometimes has a greater effect than use of a single type of epitope peptide. Thus, the peptides of the invention can be used singly or as a combination of multiple (two or more) types.

mRNA of Ep-CAM containing the peptide of the invention is expressed in lung cancer cell lines (QG56, LU99, LC99A, LC1-sq, LC65A and PC-9), large intestinal cancer cell lines, gastric cancer cell lines (MKN28, MKN45), buccal cancer cell lines (HSC-2), breast cancer cell lines, leukemia cell lines (K562), etc. Expression of Ep-CAM is also observed in tissues derived from patients with lung cancers, large intestinal cancers, gastric cancers, breast cancers or buccal cancers. Therefore, the peptide of the present invention is useful for treating or ameliorating such cancers.

The peptide of the invention, alone or in combination with various carriers, can be made into a preparation. The preparation may be in an oral or parenteral form. Generally, a parenteral form is preferable. Examples of parenteral preparations include subcutaneous injections, intramuscular injections, intravenous injections, suppositories, etc.

Oral preparations can be obtained by using pharmacologically acceptable excipients that do not inhibit the activity of the epitope peptide of the invention. Examples of such excipients include starch, mannitol, lactose, magnesium stearate, cellulose, polymerized amino acids, albumin, etc.

Parenteral preparations can be obtained by using pharmacologically acceptable carriers that do not inhibit the activity of the epitope peptide of the present invention. Examples of such carriers include water, sodium chloride, dextrose, ethanol, glycerol, DMSO, etc. Parenteral preparations may further contain albumin, wetting agents, emulsifiers, etc. as required. To stimulate cell-mediated immunity, the epitope peptide is preferably used in combination with a suitable adjuvant. The peptide of the invention can be used in a neutral or salt form. Examples of pharmacologically acceptable salts include salts of inorganic acids such as hydrochloric acid, phosphoric acid, etc., and salts of organic acids such as acetic acid, tartaric acid, etc.

The activity of the peptide of the invention can be adjusted by formulating the peptide together with compounds that, by themselves or by interaction with HLA-A2402, enhance the recognition of the peptide by CTLs, antibodies that immunologically recognize the peptide, and/or the like.

Antigen-presenting cells and major histocompatibility antigen complexes pulsed with the peptide of the present invention can also be advantageously used as cancer vaccines. The form of preparation, target patients, target cancers, effects and the like of such vaccines are the same as for cancer vaccines comprising the peptide of the present invention.

Treatment Method

The peptide, antigen-presenting cell and major histocompatibility antigen complex of the present invention, when administered to humans having HLA-A2402 as a leukocyte antigen, induce or activate Ep-CAM-specific HLA-A2402-restricted CTLs to thereby treat or ameliorate epithelial cancers.

The dosage of the peptide of the present invention varies depending on the degree of recognition of the peptide by CTLs, and may be, for example, about 0.01 mg to about 100 mg, and preferably about 0.1 mg to about 30 mg, on an active epitope peptide basis per day for an adult human. The dosage intervals can be suitably selected for individual patients depending on the purpose of administration.

Alternatively, effective cancer vaccination can be achieved by introducing, into the patient's blood circulation, a mononuclear cell fraction that has been separated from the patient's peripheral blood and cultured together with the peptide of the present invention to induce and/or activate CTLs. The culture conditions, such as the concentrations of mononuclear cells and the peptide of the invention, can be selected so as to enable administration of $10^8$ to $10^{10}$ CTLs/day to an adult human. Such conditions can be easily determined by simple tests. Substances with lymphocyte proliferation ability, such as interleukin-2, may be added during culturing.

The dosage of antigen-presenting cells is, for example, about $10^6$ to $10^9$ cells/day, and preferably $10^7$-$10^8$ cells/day, for an adult human. Effective cancer vaccination can also be achieved by introducing, to the patient's blood circulation, a co-culture of a mononuclear cell fraction separated from the patient's peripheral blood with the antigen-presenting cells of the present invention.

The dosage of the histocompatibility antigen complex is, for example, 1 to 100 mg/day, and preferably 5 to 50 mg/day, for an adult human. Further, effective cancer vaccination can be achieved by introducing, into the patient's blood circulation, a co-culture of a mononuclear cell fraction separated from the patient's peripheral blood with the major histocompatibility antigen complex of the invention.

Gene Therapy Drug for Cancers

The polynucleotide of the present invention (encompassing the complementary strand) is useful as gene therapy drugs for, for example, lung cancers, large intestinal cancers, gastric cancers, breast cancers, buccal cancers, etc.

For cancer therapy, a vector containing the polynucleotide of the invention may be directly introduced into the body, or may be introduced into cells collected from a human, the cells being then returned to the body. The vector is not limited and can be selected from those known to be usable for gene therapy, such as retroviruses, adenoviruses, vaccinia viruses, etc., among which retroviruses are preferable. Such viruses are replication defective.

The polynucleotide of the present invention may be introduced into cells by microinjection techniques in which the polynucleotide is encapsulated in a liposome and transferred.

Thus, the cancer gene therapy drug of the invention may be in any form: the polynucleotide of the invention alone, a recombinant vector containing the polynucleotide of the invention, a liposome encapsulating the polynucleotide of the invention, etc.

The dose of the polynucleotide of the invention varies depending on the degree of recognition, by CTLs, of the peptide coded by the polynucleotide. For example, a suitable dose for an adult human is, on the basis of the amount of the polynucleotide portion coding the epitope peptide of the invention, about 0.1 µg to about 100 mg/day, and preferably about 1 µg to about 50 mg/day. Such a dose can be administered once every few days to once every several months.

The polynucleotide of the invention can be used in combination with a cytokine, such as IL-2, or a substance that interacts with the polynucleotide of the invention to thereby enhance the expression of the polynucleotide.

(IX) Cytotoxic T Lymphocyte

The cytotoxic T lymphocyte of the present invention is obtained by stimulating peripheral blood lymphocyte using at least one of (a) to (d) below:

(a) peptide of the invention,
(b) antigen-presenting cell of the invention,
(c) major histocompatibility antigen complex of the invention, and
(d) major histocompatibility antigen complex tetramer of the invention The CTLs of the invention is induced by culturing peripheral blood lymphocytes together with at least one of (a) to (d) in RPMI1640 medium which preferably contains human serum, at about 37° C. for about 7 to about 14 days. When peripheral blood lymphocytes are stimulated with the major histocompatibility antigen complex (hereinafter referred to as "MHC") or tetramer thereof, the CTL is induced and combined with the MHC or tetramer. Thus, the CTL is separated from the MHC or tetramer by a suitable method.

Specifically, the CTL can be obtained, for example, by the following preparation method.

When Stimulating with Epitope Peptide or Antigen-Presenting Cells

Lymphocytes separated from peripheral blood are cultured together with the peptide of the invention or antigen-presenting cells pulsed with the peptide, in a carbon dioxide incubator at about 37° C. for about 7 to about 10 days. Then, preferably after adding IL-2, PHA, anti-CD3 antibody or the like, incubation is performed for about 7 to about 14 days to thereby stimulate and proliferate CTLs.

The stimulation with the peptide or antigen-presenting cells, optionally followed by stimulation with IL-2 or the like, is carried out about three times to thereby obtain the required number of CTLs.

The epithelial cancer-specific CTLs thus obtained can be used, for example, in the form of a suspension in human albumin-containing PBS or the like, as a passive immunotherapy drug for epithelial cancer or the like. The form of the passive immunotherapy drug is usually be an injection, such as an intramuscular injection, subcutaneous injection, intravenous infusion or the like.

When Stimulating with MHC or Tetramer Thereof

<Isolation by Staining>

Lymphocytes are separated from peripheral blood or the like, and reacted with a suitable concentration of MHC or MHC tetramer at about 4 to about 25° C. for about 30 to about 60 minutes, in, for example, PBS. A labeling dye, such as FITC or PE, is added to the reaction mixture to stain the CTLs bound to the MHC or MHC tetramer. Subsequently, the stained CTLs are isolated using a flow cytometer or microscope.

<Isolation by Immobilization of MHC>

Using a sterile plate with MHC or MHC tetramer immobilized on its surface, lymphocytes separated from peripheral blood are reacted with the immobilized MHC or MHC tetramer in the plate at about 4 to about 25° C. for about 30 to about 60 minutes. After washing away other cells, which are unbound and floating, the epithelial cancer-specific CTLs remaining on the plate are suspended in a new medium. The epithelial cancer-specific CTLs thus isolated can be stimulated with a T-cell stimulant, such as an anti-CD3 antibody, PHA, IL-2 or the like, to proliferate the CTLs into a number required for use as a passive immunotherapy drug.

<Use of Magnetic Beads>

Biotinized MHC prepared as described above is bound to streptavidin-labeled magnetic beads to prepare a conjugate (hereinafter referred to as "MHC-magnetic beads"). Subsequently, lymphocytes are separated from peripheral blood or the like, and the MHC-magnetic beads at a suitable concentration are added so that the lymphocyte:bead ratio becomes 1:5-20, followed by reaction.

When the test tube containing the epithelial cancer-specific CTLs bound to the MHC-magnetic beads is placed in a magnetic field, the CTLs bound to the beads are attracted to the test tube inner wall on the magnet side.

With the CTLs bound to the beads being adhered to the test tube internal wall, other cells are washed away. Thereafter, the test tube is removed from the magnetic field, and the antigen-specific CTLs remaining in the test tube are suspended in a new medium.

The epithelial cancer-specific CTLs thus isolated can be stimulated with a T lymphocyte stimulant, such as an anti-CD3 antibody, PHA, IL-2 or the like, to thereby proliferate the CTLs into a number required for use as a passive immunotherapy drug.

<Method for Treating or Ameliorating Cancers>

The CTL of the invention, when administered to an epithelial cancer patient as a passive immunotherapy drug, can treat or ameliorate the cancer.

The dose varies among patients depending on the purpose of administration. For example, a suitable dose for an adult human is about $10^7$ to about $10^{11}$ cells/day, and preferably about $10^8$ to about $10^{10}$ cells/day. Such a dose can be administered once every few days to once every several months.

(X) Method for Quantifying CTLs

In cancer therapy management, including appropriate use of anticancer drugs and chemotherapy drugs, it is important to know whether epithelial cancer-specific CTLs are present in peripheral blood of high-risk cancer patients (patients with lowered immunity caused by cancer cells or cancer tissues, patients with complications, elderly patients, infant patients, pregnant patients). Epithelial cancer-specific HLA-A2402-restricted CTLs can be quantified by the following method.

A method comprising the steps of causing any one of (a) to (d) below to act on a peripheral blood sample, and quantifying CTLs or cytokine(s) produced thereby in the sample:
(a) peptide of the invention,
(b) antigen-presenting cell of the invention,
(c) MHC of the invention, and
(d) MHC tetramer of the invention.

The obtained value is compared with a value quantified by the same method except for using a solution containing HLA-A2402-restricted CTLs at a known concentration, thereby calculating the HLA-A2402-restricticted CTL concentration of the peripheral blood sample.

The HLA-A2402-restricted CTLs induced by one or more of (a) to (d) or cytokine(s) produced by the CTLs can be quantified, for example as follows.

When Using Epitope Peptide

Lymphocytes separated from peripheral blood are stimulated with the peptide of the invention, and the number of the induced CTLs or the amount of cytokine(s) (which encompasses chemokines), such as interferon-γ (IFN-γ), interleukin or the like, produced by the CTLs is measured. A specific method is described below, taking the case of IFN-γ as an example.

<Quantification of Intracellular IFN-γ-Producing Cells>

Lymphocytes separated from peripheral blood are suspended in RPMI1640 medium containing 10% human serum at a cell concentration of $2\times10^6$/ml, and the CTL epitope peptide of the invention is added at a concentration of 1 mg/ml. Further, an intracellular protein transport inhibitor, such as Brefeldin A, is added, followed by culturing in a carbon dioxide incubator at 37° C. for 5 to 6 hours. After culturing, the cells are immobilized, subjected to membrane permeabilization treatment and reacted with a fluorescent-labeled anti-IFN-γ antibody. The IFN-γ positive cells in CD8 positive lymphocytes are quantified using a flow cytometer or the like.

<Quantification of CD8 Positive Cells>

Labeled CD8 positive cells can be quantified by following the above method of quantifying intracellular IFN-γ-producing cells except for using an anti-CD8 antibody in place of the fluorescent-labeled anti-IFN-γ antibody.

<Quantification of Cytokine(s) (ELISPOT Assay)>

A 96-well MultiScreen-HA plate (Millipore) is coated overnight at 4° C. with an anti-IFN-γ monoclonal antibody. After washing the wells with PBS, lymphocytes separated from peripheral blood are inoculated into the wells. The epitope peptide is placed into the wells and cultured in a 5% $CO_2$ incubator at 37° C. for 20 hours. On the following day, the plate is washed with PBS containing 0.05% Tween-20, and reacted at room temperature with anti-IFN-γ rabbit serum for 90 minutes and then with peroxidase-labeled anti-rabbit IgG goat serum for 90 minutes. Further, 0.1 M sodium acetate buffer (pH 5.0) containing 3-amino-9-ethylcarbazole (Sigma) and 0.015% hydrogen peroxide solution is placed into the wells and reacted at room temperature for 40 minutes. The IFN-γ spots are visualized and counted with a stereoscopic microscope.

<Method of Quantifying Cytokine(s) Secreted in Culture Supernatant>

Lymphocytes separated from peripheral blood are suspended in RPMI1640 medium containing 10% human serum, at a cell concentration of $2 \times 10^6$ cells/ml, and the CTL epitope peptide of the invention is added at a concentration of 1 μg/ml. Culturing is performed in a carbon dioxide incubator at 37° C. for 24 to 48 hours. After culturing, the supernatant is collected, and the IFN-γ concentration in the supernatant is measured using a commercially available ELISA kit (e.g., HUMAN IFN gamma ELISA from ENDOGEN).

When Using MHC Tetramer

Lymphocytes are separated from peripheral blood or the like, and reacted with an MHC tetramer (fluorescently labeled with streptavidin) at a concentration of 1 to 100 μg/m, at 37° C. for 15 minutes. The CTLs bound to MHC are stained by adding an antibody that binds to the CLT bound to MHC, the antibody being labeled with another fluorescent dye. The stained CTLs can be counted using a flow cytometer or microscopy.

EXAMPLES

Hereinafter, the present invention will be described in more detail with reference to Examples, but is not limited thereto.

Example 1

1) Donors and Cell Lines

All donors were made fully aware of the research program and its purpose approved by the Ethics Committee of the Aichi Cancer Center. Peripheral blood samples for testing were obtained from five HLA-A2402 positive healthy donors after informed consent. From the peripheral blood samples obtained from each donor, peripheral blood mononuclear cells (PBMCs) were isolated by Ficoll density gradient centrifugation.

A large cell carcinoma cell line LU 99 (JCRB0080) as a human lung cancer cell line; a human epidermoid carcinoma cell line HSC-2 (JCRB0622); epidermoid carcinoma cell lines MKN28 (JCRB0253) and MKN45 (JCRLB0254) as a human gastric cancer cell line; and an epidermoid carcinoma cell line COLO320DM (JCRB0225 or ATCC:CCL-220) as a human colorectal cancer cell line were purchased from the JCRB Cell bank (Ministry of Health, Labour and Welfare: Cellbank.nihs.go.jp). An epidermoid carcinoma cell line LC-1/sq (RCB0455) as a human lung cancer cell line was purchased from the Riken cell bank.

The LC/sq cells were maintained in a 45% RPMI1640 culture medium and a 45% Ham's F12 culture medium (product of Sigma), which was prepared by adding a liquid nutrition supplement, comprising 10% FCS, L-glutamine, penicillin, streptomycin, and kanamycin. The COLO320DM cells and MKN28 were maintained in a DMEM culture medium (product of Sigma). The K562 cells were maintained in an IMDM culture medium (product of Sigma), which was prepared by adding a liquid nutrition supplement, comprising 10% FCS (fetal calf serum, product of Life Technology), L-glutamine, penicillin, streptomycin, and kanamycin.

Other cancer cell lines were cultured in a RPMI1640 culture medium, which was prepared by adding a liquid nutrition supplement, comprising a 10% FCS, $2 \times 10^{-3}$ M L-glutamine, 100 U/ml penicillin, 100 μg/ml streptomycin, 100 μg/ml kanamycin, and $5 \times 10^{-5}$ M β-mercaptoethanol (as a complete medium).

The HLA-A2402 gene was introduced into 174CEM.T2 (hereinafter referred to as a "T2 cell"), giving cells presenting an HLA-A2402 binding peptide (hereinafter referred to as "T2-24 cell") as peptide-presenting cells. T2-24 cells were cultured in an IMDM culture medium (Iscove's modified Dulbecco's medium: product of Gibco) containing 10% fetal calf serum, L-glutamine, penicillin, streptomycin, and G418 (product of Gibco).

According to the method described in Tissue Antigens, 59:502-511, (2002), an HLA-A2402-negative QG56 cell line and an HLA-A2402-negative A549 (JCRB0076) cell line were infected with retroviruses encoding HLA-A2402. In order to detect the infected cells, the infected QG56 cells were maintained in a complete medium containing puromycin with a final concentration of 0.6 μg/ml, and designated QG56-A24. Similarly, the infected A549 cells were maintained in a complete medium containing puromycin with a final concentration of 0.9 μg/ml, and designated A549-A24.

2) Peptide Synthesis

Potential HLA-A2402-binding peptides within Ep-CAM (accession number: M33011) were identified by computer-based prediction according to the HLA Peptide Binding Prediction Program based on the estimated half-time dissociation of HLA peptide complexes available at the World Wide Website Bioinformatics & Molecule Analysis Section (BI-MAS:BioInfomatics and molecular analysis section) (bimas-.dcrt.gov/molbio/hla_bind).

Seven peptides selected based on the Ep-CAM epitope peptide prediction results were synthesized by PepSet (product of Mimotope). As necessary, the resultants were dissolved in 100 μL of dimethyl sulfoxide, and further diluted to 0.1 M (pH 7.4) in 40% acetonitrile.

The production amount of each peptide was estimated to be 1 μmol.

The seven synthetic peptides were designated Ep31, Ep173, Ep185, Ep250, Ep225, Ep296, and Ep304, respectively. Table 1 shows the synthesized peptide sequences of the Ep-CAMs.

TABLE 1

| Peptide name | Amino acid sequence | Amino acid positions | Amino acid length | Score[a] | % MFI increase[b] |
|---|---|---|---|---|---|
| $Ep_{31}$ | NYKLAVNCF (SEQ ID NO:3) | 31-39 | 9 | 120 | 85 |
| $Ep_{173}$ | RYQLDPKFI (SEQ ID NO:1) | 173-181 | 9 | 150 | 102 |

TABLE 1-continued

| Peptide name | Amino acid sequence | Amino acid positions | Amino acid length | Score[a] | % MFI increase[b] |
|---|---|---|---|---|---|
| $Ep_{185}$ | LYENNVITI (SEQ ID NO:4) | 185-193 | 9 | 75 | 79 |
| $Ep_{225}$ | LFHSKKMDL (SEQ ID NO:5) | 225-233 | 9 | 20 | 29 |
| $Ep_{250}$ | YYVDEKAPEF (SEQ ID NO:2) | 250-259 | 10 | 198 | 57 |
| $Ep_{296}$ | KYEKAEIKEM (SEQ ID NO:6) | 296-305 | 10 | 83 | 24 |
| $Ep_{304}$ | EMGEMHREL (SEQ ID NO:7) | 304-312 | 9 | 5 | 16 |

Notes:
[a]Estimated half-time of dissociation from HLA-A24 molecules (minutes), obtained by accessing the World Wide Web site BioInformatics and Molecular Analysis Section (BIMAS) HLA Peptide Binding Predictions
[b]The synthetic peptides were evaluated for their binding activity to HLA-A24 molecules based on an MHC stabilization assay. % MFI indicates mean fluorescence intensity.

Separately, human immunodeficiency virus-1 (HIV-1) envelope peptide RYLRDQQLL (SEQ ID NO:13) (designated ENV584, J. Immunol, 159:6242-6252, 1997: residues 584-592) and EBV latent membrane protein 2 peptide (EBV latent membrane) (designated EBV-LMP 419, J. Immnol, 158:3325-3334, 1997: residues 419-427) were synthesized as controls (Toray Industries research center company).

3) Cell Staining and a Flow-Cytometry Analysis

Testing was conducted using an indirect immunofluorescent antibody assay using a monoclonal antibody against HLA-A2402 expressed on the cell surface (product of One Lambda, Inc) and FITC labeled anti-mouse IgG(ab')$_2$ fragments (product of Immunotech). MHC/peptide tetramer was prepared according to the procedure described in "Blood, 98:1872-1881, 2001, Science, 274:94-96, 1996".

CD8 positive T cell line or its clone were stained with phycoerythrin (phycoerythrin: PE)-labeled HLA-A2402 tetramer containing Ep-CAM peptide and Ep173 (referred to as HLA-A2402/Ep173 tetramer), or containing HIV-1 peptide and ENV584 (referred to as an HLA-A2402/ENV584 tetramer).

The flow-cytometry analysis of the stained cell was carried out using FACSCalibur (product of Becton, Dickinson and Company), and data were analyzed using CellQuest software (product of Becton, Dickinson and Company).

MHC Stabilization Assay

For the evaluation of the HLA-A2402 binding efficiency of the synthetic peptides, an MHC stabilization assay was conducted using T2-A24 cells (cell line in which the plasmid expressing HLA-A2402 molecules was transfected to T2[174×CEM.T2:ATCC accession number: CRL-1992]) according to the procedure of Kuzushima et al. (Blood, 98:1872-1881, 2001).

To be specific, each peptide with a concentration of 10 μM was incubated at 26° C. for 16 hours in a 200 μL RPMI1640 culture medium containing T2-A24 cells (2×10$^5$ cells), 0.1% FCS, and 5×10$^{-5}$ M β-mercaptoethanol, followed by a further incubation at 37° C. for 3 hours. After incubation, cell-surface HLA-A2402 molecules were stained with an anti-HLA-A2402 monoclonal antibody and the FITC-labeled antibody of (3) above. The expression level was determined by FACSCalibur and the mean fluorescence intensity (MFI) was recorded.

The % MFI increase was calculated by the following formula:

% MFI increase=100×(MFI of group administered with peptide−MFI of group not administered with peptide)/(MFI of group not-administered with peptide).

Table 1 shows the results concerning the % MFI level increases. As shown in Table 1, HLA-A2402 expression level on the cell surface was increased for most peptides, which shows that these peptides are bound to the cell surface, and thus MHC is stabilized.

In particular, among the above peptides, Ep173 (RYQLD-PKFI) showed the highest affinity for the HLA-A2402. Ep304 (EMGEMHREL), which showed the lowest affinity, was not subjected to further experiments.

5) Production of Ep-CAM Peptide-Specific CTL and Clones Thereof

Peripheral blood monocyte-derived dendritic cells (DCs) were produced according to the procedure of Dauer et al. (J. Immunol, 170:4069-4076).

More specifically, cells adherent to plastic were isolated from peripheral blood mononuclear cells of HLA-A2402 positive healthy volunteers, and cultured in a RPMI1640 medium containing 5% heat-inactivated human blood serum, 10 μg/mL recombinant human interleukin-4 (hIL-4, product of R&D systems company), and 50 ng/mL recombinant human/granulocyte-macrophage colony stimulating factor (hGM-CSF, product of R&D systems company). After one day of incubation, 50 ng/mL IL-1β (product of PeproTech, Inc.), 50 ng/mL recombinant human/tumor necrosis factor-α (hTNF-α: product of PeproTech, Inc.), and 1 μM prostaglandin E2 (product of Cayman Chemical Company) were added for cell growth. After 2 or 3 days passed, the cells were harvested for use in a monocyte-derived dendritic cells for antigen presentation.

The produced cells apparently expressed dendritic cell-mediated antigens such as CD1a, CD80, CD83, CD86, and HLA class II molecules.

Separately, using CD8 microbeads (product of Milteny Biotec), CD8 positive T lymphocytes were isolated from the same donors.

Subsequently, self-derived dendritic cells were pulsed at room temperature for 2 to 4 hours with each of the Ep-CAM synthesis peptides with a concentration of 10 μM in an AIM-V culture medium (product of Gibco) containing $5 \times 10^{-5}$ M β-mercaptoethanol, followed by irradiation (33Gy).

The dendritic cells ($1 \times 10^5$ cells) were then cocultivated in a culture tube with CD8 positive T lymphocytes ($1 \times 10^6$ lymphocytes) in a RPMI1640 culture medium containing 10% human blood serum, 25 ng/mL recombinant human IL-7 (product of R&D systems company), and 5 ng/mL recombinant human IL-12 (product of R&D systems company).

After seven days of cultivation, the cells were stimulated by adding $1 \times 10^5$ peptide-pulsed self-derived dendritic cells prepared as above. After a further seven days of cultivation, the cells were stimulated 3 times by the same procedure. After each restimulation, human recombinant IL-2 (product of Takeda Pharmaceutical Company, Ltd.) was added to give a final concentration of 20 units/ml. Actively proliferating cells were divided into 2 or 3 tubes as necessary, and cultured in a fresh culture medium containing 20 units/ml of IL-2.

The T-cell specificity was examined by ELISPOT assay.

In order to establish T-cell clones, limiting dilution of polyclonal CTL was performed according to the method described in Blood, 98:1872-1881, and 2001. More specifically, polyclonal CD8 positive T-cells were seeded in a 96-well circular plate (1, 3, 10 cells/well) containing a culture medium (0.2 ml) together with anti-CD3 monoclonal antibodies (30 ng/ml), product of Orth Diagnostic Inc., IL-2 (50 U/ml), $1 \times 10^5$ cells of γ-irradiated (33 Gy) PBMCs, and $2 \times 10^4$ cells of γ-irradiated (55 Gy) B lymphoblast cells transformed by EBVs (cells obtained by transforming volunteers' peripheral blood B lymphocytes with a 95.8-cell (JCRB9123) supernatant).

After two weeks of incubation, the specificity of the proliferated cells was determined by a CTL-CTL-killing assay in the same manner as the method of Lee et al. (J. Immunol, 158:3325-3334, 1997).

CTL clones were incubated overnight only in a 100 μl complete culture medium or in a 96-well circular plate (300 cells/well) containing peptide of the same origin derived from Ep-CAM or control peptide ENV584 at a final concentration of 2 μM.

The cell-killing ability of CTL cells was determined on the next day using an inverted microscope. These clones showing cell-killing abilities only when pulsed with Ep-CAM were moved into a flask, and were proliferated as described above.

6) ELISPOT Assay of IFN-γ

A flat-bottom 96-well MultiScreen-HA plate (product of Millipore Corp.) with a cellulose nitrate film was coated with 10 μg/mL of anti-IFN-γ monoclonal antibody (product of R&D systems company), and incubated at 4° C. overnight. After washing with PBS (phosphate buffered saline), the plate was blocked with culture medium at 37° C. for 1 hour. In each plate well, T2-A24 cells ($5 \times 10^4$ cells) were pulsed with each epitope candidate synthetic peptide in 100 μL of RPMI1640 medium containing with 0.1% FCS and $5 \times 10^5$ M β-mercaptoethanol at room temperature for 30 minutes. $1 \times 10^5$ CD8-positive T cells suspended in the medium containing 20% FCS were seeded to each well.

$1 \times 10^4$ CD8 positive T-cells were used as responding cells when there were too many spots to count. The entire measurement process was conducted in duplicate.

The plate was incubated at 37° C. for 20 hours in a 5% $CO_2$ incubator, and thoroughly washed with PBS containing 0.05% Tween 20. Subsequently, polyclonal rabbit anti-IFN-γ antibody (product of Genzyme) was added to each well, left at room temperature for 90 minutes, and then exposed to peroxidase-conjugated sheep anti-rabbit anti-immunoglobulin G (product of Genzyme) for a further 90 minutes. For visualization of IFN-γ specific spots, 0.1 M sodium acetate buffer (pH 5.0) containing 3-amino-9-ethylcarbazole (product of Sigma) and 0.015% hydrogen peroxide solution was added to each well. After 40 minutes, the reaction was stopped by washing with water, and the plate was dried. The number of diffused large spots was counted under the microscope.

Figure 2:
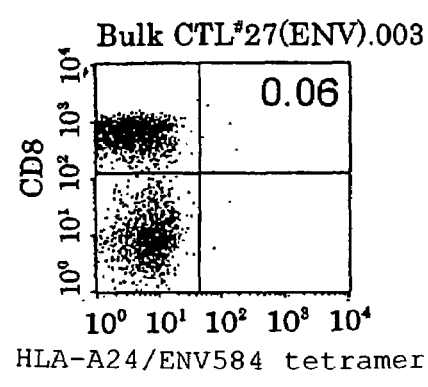
FIG. 2 shows the tetramer-staining results of Ep-CAM peptide specific polyclonal (A) and monoclonal (B) CTLs.
Figure 2:
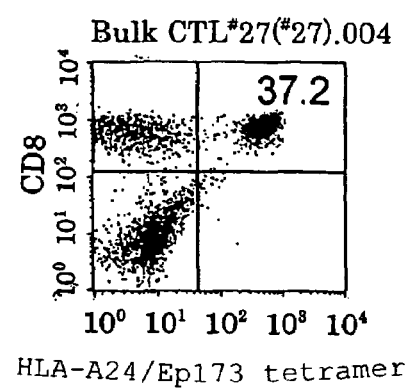
Figure 2:
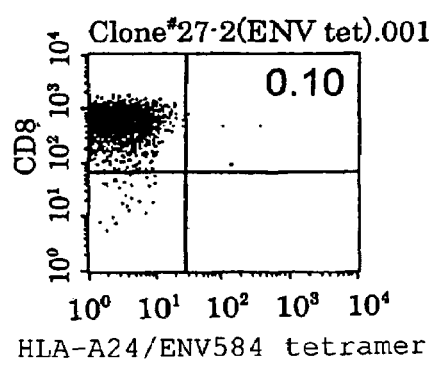
Figure 2:
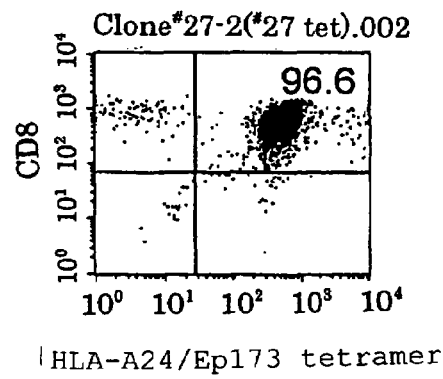

The results are shown in FIGS. 1 and 2.

FIG. 1 shows the ELISOT assay evaluation results of the polyclonal peptide-activated cytotoxic lymphocyte cell lines when CD8 positive T-cells of five HLA-A2402 positive healthy donors were stimulated by self-derived dendritic cells pulsed by one of each of the six peptides.

As can be seen from FIG. 1, when the CD8 positive T-cells of five HLA-A2402 positive healthy donors were stimulated by the self-derived dendritic cells pulsed by one of each of the six peptides, the T-cell lines obtained from four donors showed predominant production of IFN-γ spots by incubation with T2-A24 cell pulsed by Ep173.

The CTL line subjected to Ep250 stimulation obtained from the donor No. 3 specifically produced IFN-γ spots by incubation with Ep250.

FIG. 2 shows the tetramer-staining results of Ep-CAM peptide specific polyclonal and monoclonal CTLs.

FIG. 2A shows that polyclonal CD8 positive T-cells stimulated 4 times with Ep173 were stained with FITC-labeled anti-CD8 antibody, PE-labeled HLA-A24 tetramer containing Ep173, or a control peptide ENV584, and were analyzed by flow cytometry. The proportion of tetramer positive cells among the total CD8 positive T-cells is shown as a percentage in the upper right.

As shown in FIG. 2A, IFN-γ spot formation was not observed in most control peptides, ENV584. After four stimulations, the CTL lines established from donor No. 4 were specifically stained with the HLA-A24/Ep173 tetramer but not with the HLA-A24/ENV584 tetramer (37.2%:0.06% with respect to the total CD8 positive T-cells, FIG. 2A).

FIG. 2B shows that Ep173-specific CTL clones (C27), were stained in the same manner as above. The proportion of tetramer positive cells among the CD8 positive T-cells is shown as a percentage in the upper right.

As shown in FIG. 2B, the intensity of tetramer positive cells was equivalent to or higher than that of tetramer negative cells by 2- to 3-fold on a logarithmic scale. The inventors established a T-cell clone, C27 from the limiting dilution culture medium of the Ep173 specific polyclonal CTL line of donor No. 4.

This research using tetramers shows that both polyclonal and monoclonal Ep173-specific CD8 positive T-cells have high-affinity cell receptors specific for HLA-A2402/Ep173 complexes.

Accordingly, Ep173-specific CTL clones were established from this CTL line.

Example 2

Properties of Peptide Ep173 Specific CTL Clones, Part 1

7) CTL Assay

The inventors further examined whether C27 recognizes peptide spontaneously presented on the surface of tumor cells in the context of HLA-A24.

Chromium-labeled cells were incubated with monoclonal antibodies specific for any one of total HLA class I, HLA- A24, or HLA-A2 before addition of C27, and the CTL assay was performed at an effector to target ratio of 10.

The target cells (PC9 cells) were labeled with chromium ($^{51}$Cr) in 100 μl of culture medium at 37° C. for 1 hour. In some experiments, in order to specify HLA restriction, a predetermined amount of blocking antibody W6/32 (anti-HLA class I), MA2.1 (anti-HLA-A2), and A11.1 (anti-HLA-A24) were added to each well 30 minutes prior to the addition of effector cells.

The plate was incubated at 37° C. for 4 hours, and the supernatant was counted using a γ-counter.

The percent specific $^{51}$Cr release was calculated according to the formula: 100×(experimental release–spontaneous release)/(maximum release–spontaneous release).

Figure 3:
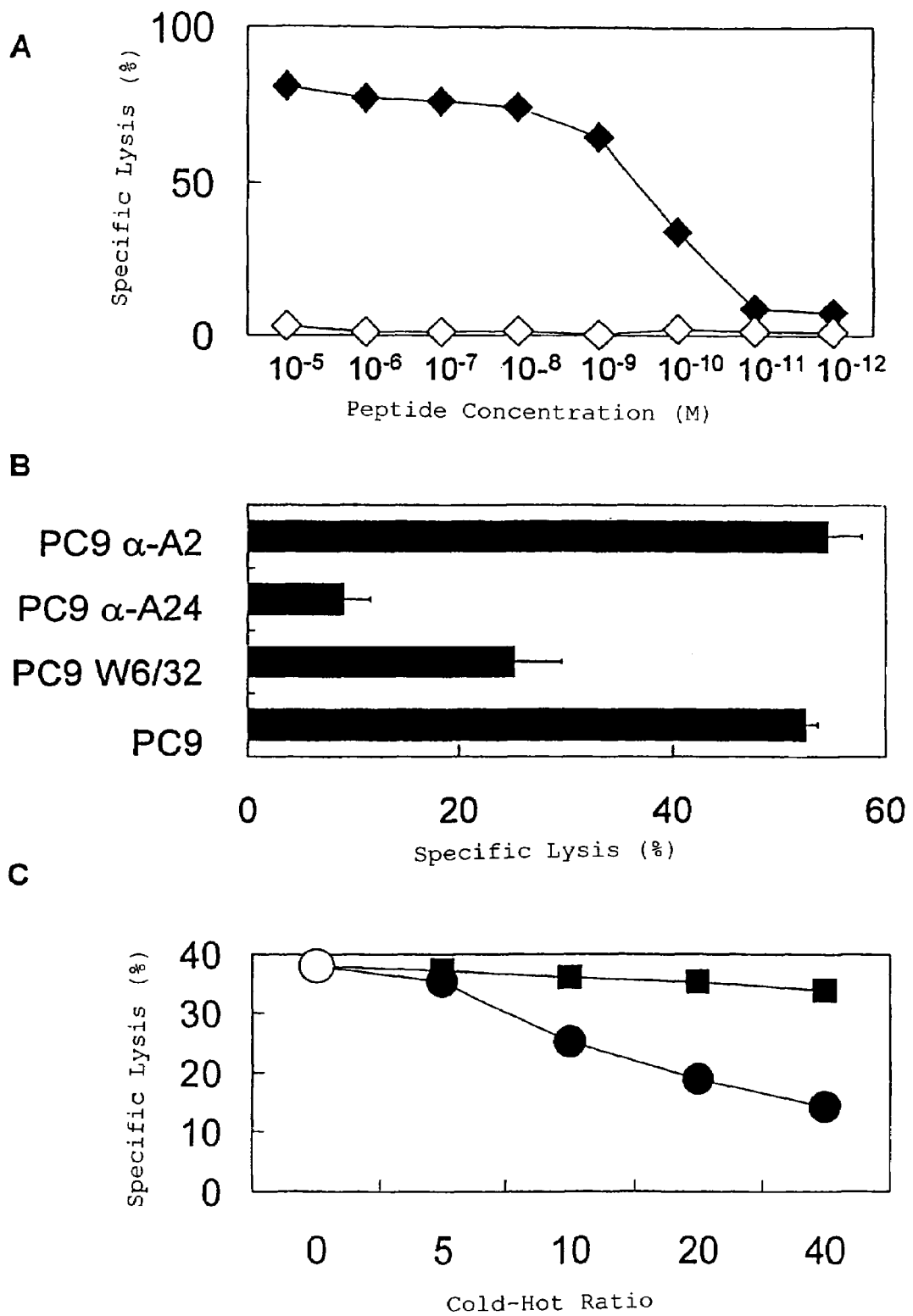
FIG. 3 shows Ep173-specific-CTL-clone characteristics.
Figure 5:
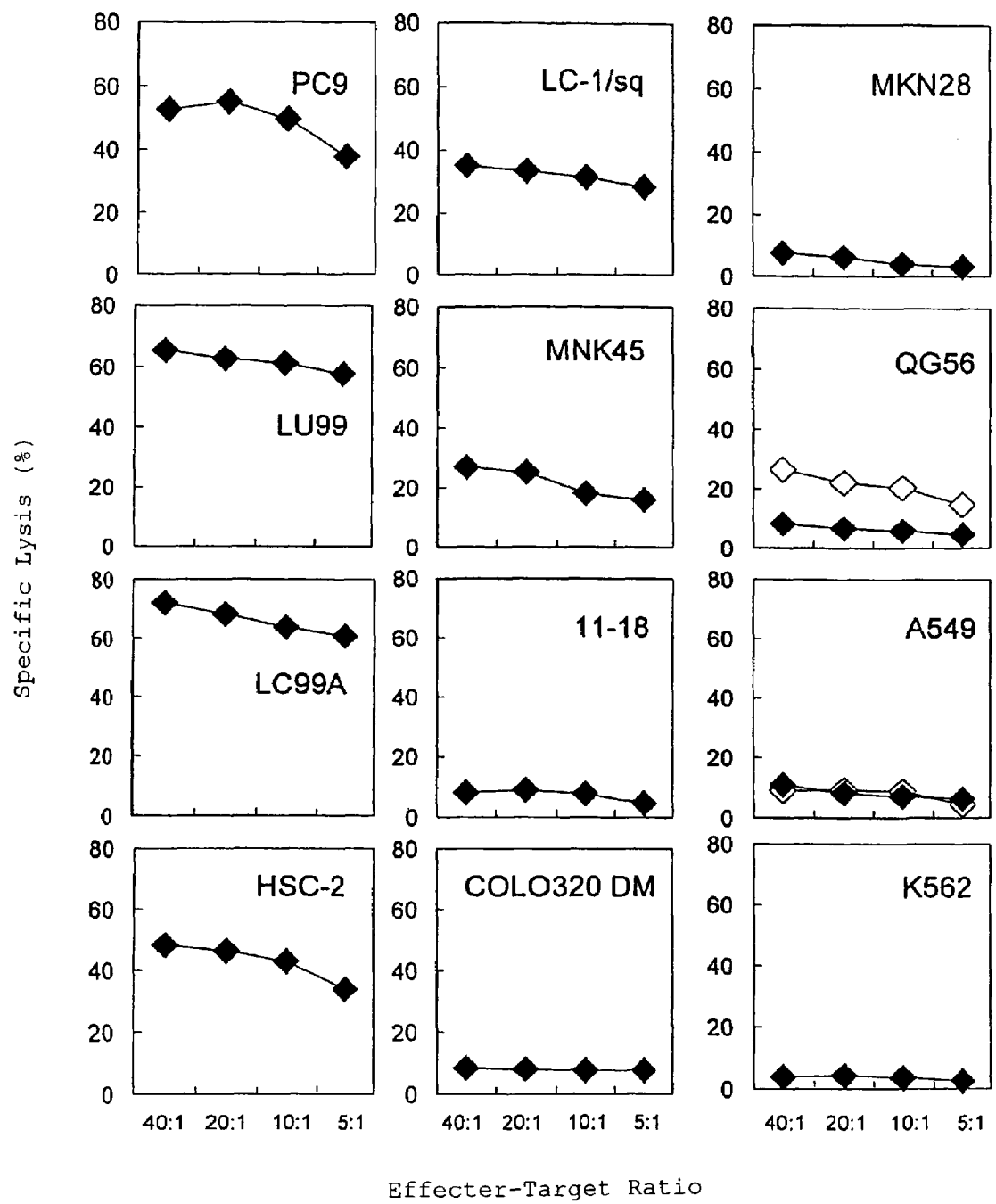
FIG. 5 shows the cytotoxicities of the Ep173-specific CTL clone (C27) against various cancer cell lines.

The results are shown in FIGS. 3 and 5.

FIG. 3A shows the cytotoxicity of C27 (Ep173-specific CTL clones) against T2-A24 at each indicated concentration of peptide Ep173 and control peptide EBV-LMP419 determined by $^{51}$Cr release assay at an effector to target ratio of 1.

Consequently, Ep173-specific CTL clones (C27) demonstrated a cytotoxicity against T2-A24 cells pulsed with Ep173 at a low peptide concentration of 100 pM, while such cytotoxicity was not observed with EBV-LMP419 (control peptide).

FIG. 5 and Table 2 show the evaluation results of the cytotoxicity of C27 against various cancer cell lines.

TABLE 2

|  | Origin | Ep-CAM RT-PCR | HLA-A24 (MFI[a]) |
|---|---|---|---|
| Lung cancers |  |  | + (87.16) |
| Lu99 | large cell carcinoma | + | + (43.53) |
| PC9 | adenocarcinoma | ++ | + (73.67) |
| 11-18 | adenocarcinoma | − | + (96.71) |
| LC99A | large cell carcinoma | + | − (3.67) |
| LC65A | small cell carcinoma | + | + (70.56) |
| LC-1/sq | squamous cell cancer | + | − (3.21) |
| A549 | adenocarcinoma | − | + (109.73) |
| A549-A24 | adenocarcinoma | N.D.[b] | − (2.65) |
| QG56 | squamous cell cancer | + | +(84.12) |
| QG56-A24 | squamous cell cancer | N.D. |  |
| Gastric cancers |  |  |  |
| MKN28 | adenocarcinoma | + | − (7.67) |
| MNK45 | adenocarcinoma | + | + (47.99) |
| Colon cancers |  |  |  |
| COLO320 DM | adenocarcinoma | − | + (35.35) |
| Other cancers |  |  |  |
| HSC-2 | oral squamous cell cancer | ± | + (34.40) |
| K562 | leukemia | ± | − (5.23) |
| T2-A24 | B × T hybrid cell | − | + (197.75) |

Notes:
[a]The mean fluorescence intensity was evaluated by immunofluorescence using HLA-A24mAb and FITC labeled anti-mouse IgG antibody F (ab')$_2$ fragments.
[b]Not done FIG. 2 shows the evaluation result of the cytotoxicity of C27 (Ep173-specific CTL clone) for eight types of HLA-A24 positive cancer cell lines and an HLA-A24 negative cell line as target cells.

All cell lines expressed Ep-CAM, except lung adenocarcinoma cell lines 11-18, COLO320DM, and A549. HLA-A2402 genes were transformed like a retrovirus into A549 and QG56, and the transformants designated A549-A24 and QG56-A24 were also used as target cells. The cytotoxicity was specified by $^{51}$Cr release assay at each effector:target ratio (40:1, 20:1, 10, 1, 5:1). K562 is a typical cell line sensitive to natural killer cells.

As shown in FIG. 5 and Table 2, C27 effectively exert toxicity to lung cancer cell lines PC9, LU99, LC-1/sq, and LC99A; oral squamous carcinoma cell line HSC-2; and gastric cancer cell lines MKN45 expressing both HLA-A24 and Ep-CAM. However, C27 demonstrated no toxicity against HLA-A24 positive Ep-CAM negative cell lines (A549-A24 and COLO320DM), or HLA-A24 negative and Ep-CAM positive cell lines or Ep-CAM negative cell lines (OG56, A549, MNK28). When the HLA-A2402 gene was introduced into the HLA-A24 negative QG56 cell line (QG56-A24), C27 killed the target cells. The cytotoxicity to K562 was low.

These data demonstrated that Ep173-specific CTL kills tumor cells expressing both HLA-A24 and Ep-CAM.

FIG. 3B shows the inhibitory effect of anti-HLA-A24 monoclonal antibodies on the cytotoxicity of Ep173-specific CTL clones (C27) against the HLA-A2402 positive cell line (PC9).

The cytotoxicity of C27 against PC9 as a lung cancer cell line (HLA-A24 positive Ep-CAM positive lung cancer cell line) was blocked by monoclonal antibodies specific for HLA-A24 or class I molecules (W6/32) but was not blocked by anti-HLA-A2 monoclonal antibodies.

8) Cold Target Inhibition Assay

Cold target inhibition assay was carried out according to the method of Arai et al. (Blood, 97:2903-2907, 2001).

T2-A24 cells were incubated with epitope peptides Ep173 or EBV-LMP419 at a final concentration of $1 \times 10^{-5}$ M for 1 hour.

After several washings, the resultants were incubated with $2 \times 10^4$ effector cells for 1 hour to yield a ratio of peptide-pulsed T2-A24 cells to target cells of 40:1, 20:1, 10:1, and 5:1. $2 \times 10^3$ $^{51}$Cr-labeled PC9 cell lines were added to each well.

The cytotoxicity was determined as described in the item 7) regarding CTL assays.

FIG. 3C shows the cold target inhibition assay results.

In FIG. 3C, the abscissa represents the number ratio of T2-A24 cells (cold) pulsed with Ep173 (●) or control EBV-LMP419 (■) peptide to chromium labeled PC9 cells (hot). The ordinate represents the cytotoxicity of C27 against PC9 as a percentage. The open circle shows the cytotoxicity without a cold target.

As a result, C27-mediated cytotoxicity against PC9 was specifically inhibited by the presence of Ep173-pulsed T2-A24 cells, but was not inhibited by non-related peptides.

Thus, C27-mediated cytotoxicity against PC9 was blocked by anti-HLA-A24 monoclonal antibody or Ep173-pulsed cold target cells. Accordingly, it is demonstrated that CTL clones have an excellent specificity for Ep173 spontaneously presented on the surface of tumor cells.

Example 3

Properties of Peptide Ep173 Specific CTL Clones, Part 2

9) RT-PCR

All RNAs were extracted from a cultivated cell line using GenElute mRNA Miniprep kit (product of Sigma). Gene specific oligonucleotide primer was synthesized by Proligo (product of Proligo Japan) for use in evaluation of mRNA expression of Ep-CAM. Primers for use in RT-PCR were as follows:

Forward primer:
ATGGCGCCCCCGCAGGTCCT (SEQ ID: No. 8)

Reverse primer:
TTATGCATTGAGTTCCCTATGCATCTCACC. (SEQ ID: No. 9)

RT-PCR was carried out using a thermal cycler (product of Perkin-Elmer), and the PCR products were analyzed by 1.5% gel electrophoresis and ethidium bromide visualization.

PCR was conducted by 1 cycle of 94° C. for 5 minutes; 30 cycles of 94° C. for 30 seconds, 58° C. for 30 seconds, and 72° C. for one minute; and 1 cycle of 72° C. for 7 minutes.

10) Western Blotting Analysis

Western blotting analysis was conducted by slightly modifying the procedure of Schwartz et al. (J. Immunol, 165:768-778, 2000). More specifically, cells were dissolved in a dissolution buffer (50 mM Tris/hydrochloric acid, pH 7.5, 5 mM magnesium chloride, 1 mM EDTA, 0.5% triton X-100, 10 μM leupeptin, 2.8 μM pepstain, and 0.85 mM phenylmethanesulfonyl fluoride) at 4° C. for 30 minutes. In order to determine the protein concentration, the dissolved cells supernatant was quantitated at a wavelength of 280/260 nm. 130 μg of protein was further added to 12% SDS-PAGE. Proteins were blotted on an Immobilon-P membrane (product of Millipore), and blocked at 4° C. overnight with PBS containing 100% low fat dried milk and 0.1% Tween 20.

Searching was conducted with an Ep-CAM specific monoclonal antibody (product of LabVision), and detecting was conducted with peroxidase-conjugated sheep anti-mouse IgG (product of Zymed).

Proteins were visualized using an ECL Western blotting detection system (product of Amersham bio-sciences company).

Figure 4:
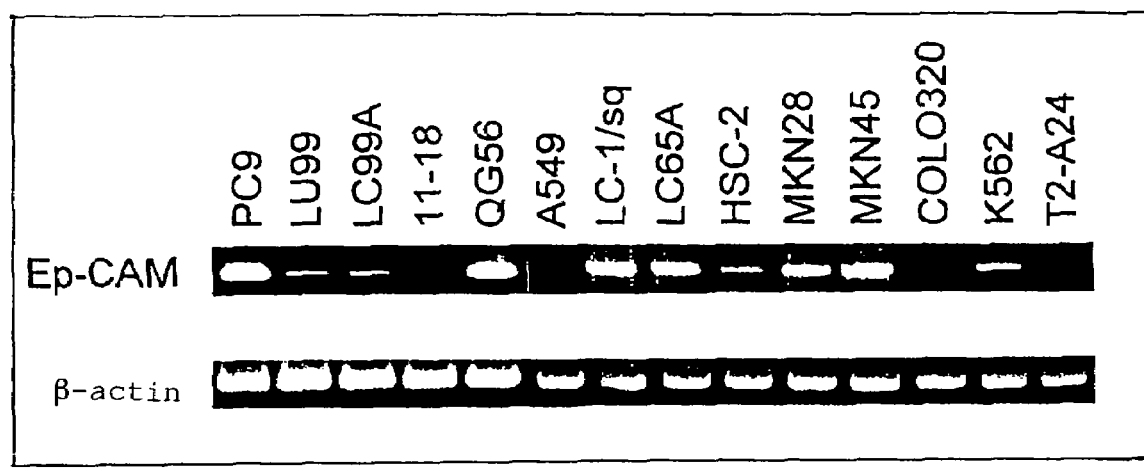
FIG. 4 shows the PCR-based Ep-CAM analysis.

FIG. 4 shows the examination results for Ep-CAM expression of cancer cell lines by RT-PCR and Western blotting analysis.

Twelve lines (80%) of 15 types of cancer cell lines apparently expressed Ep-CAM. The expression of HLA-A24 was examined by Indirect Immunofluorescence testing using anti-HLA-A24 monoclonal antibodies. Ten cell lines among the examined 15 cancer cell lines showed positive HLA-A24 expression.

As demonstrated by Examples above, the inventors have obtained novel HLA-A2402-restricted epitopes derived from Ep-CAM. At least epitope peptide, Ep173, (RYQLDPKFI; SEQ ID: No. 1) is capable of inducing CTL including a high affinity T-cell receptor specific for HLA-A2402/peptide complex, and thus immunotherapy using this peptide can be expected.

INDUSTRIAL APPLICABILITY

The peptides of the invention can be suitably used as a cancer vaccine for a wide range of HLA-A2402-containing human carcinomas.

The invention claimed is:

1. An isolated peptide of either (1) or (2) below:
   (1) a peptide consisting of the amino acid sequence represented by SEQ ID NO: 1;
   (2) a peptide consisting of the amino acid sequence represented by SEQ ID NO: 2.

2. A composition comprising the peptide of claim 1 as an active ingredient and carriers.

3. The composition of claim 2 which is used for a human having HLA-A2402 as a leukocyte antigen, and pharmacologically acceptable carriers.

* * * * *

UNITED STATES PATENT AND TRADEMARK OFFICE
CERTIFICATE OF CORRECTION

PATENT NO. : 7,619,058 B2  Page 1 of 1
APPLICATION NO. : 10/586852
DATED : November 17, 2009
INVENTOR(S) : Kiyotaka Kuzushima It is certified that error appears in the above-identified patent and that said Letters Patent is hereby corrected as shown below:

Title Page, Item (73) should read:
(73) Assignees: Aichi Prefecture, Aichi (JP); Otsuka Pharmaceutical Co., Ltd., Tokyo (JP)

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,619,058 B2
APPLICATION NO. : 10/586852
DATED : November 17, 2009
INVENTOR(S) : Kiyotaka Kuzushima It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 567 days.

Signed and Sealed this

Tenth Day of August, 2010

David J. Kappos
*Director of the United States Patent and Trademark Office*